(12) United States Patent
de Gheldere et al.

(10) Patent No.: US 7,425,304 B2
(45) Date of Patent: *Sep. 16, 2008

(54) PROCESSING SET AND METHODS FOR PROCESSING AND TREATING A BIOLOGICAL FLUID

(75) Inventors: Serge de Gheldere, Hoeilaart (BE); Mahmood Mohiuddin, Hawthorn Woods, IL (US); Peyton S. Metzel, Libertyville, IL (US); George D. Cimino, Lafayette, CA (US); Derek J. Hei, Concord, CA (US); Michael S. Clarke, San Francisco, CA (US)

(73) Assignees: Fenwal, Inc., Lake Zurich, IL (US); Cerus Corporation, Concord, CA (US)

( * ) Notice: Subject to any disclaimer, the term of this patent is extended or adjusted under 35 U.S.C. 154(b) by 26 days.

This patent is subject to a terminal disclaimer.

(21) Appl. No.: 11/353,397

(22) Filed: Feb. 13, 2006

(65) Prior Publication Data

US 2006/0197031 A1 Sep. 7, 2006

Related U.S. Application Data

(62) Division of application No. 09/325,599, filed on Jun. 3, 1999, now Pat. No. 7,025,877.

(51) Int. Cl.
*G01N 21/00* (2006.01)

(52) U.S. Cl. .............. 422/63; 422/64; 422/65; 422/100; 422/101; 422/102; 210/94; 210/202; 210/335; 604/4.01; 604/5.01; 604/6.01

(58) Field of Classification Search ........... 422/99–102, 422/63–65; 604/4–6; 210/94, 202, 335
See application file for complete search history.

(56) References Cited

U.S. PATENT DOCUMENTS

| 3,211,368 A | 10/1965 | Shanley |
| 3,221,741 A | 12/1965 | LeVeen |
| 3,692,493 A | 9/1972 | Terasaki |

(Continued)

FOREIGN PATENT DOCUMENTS

AU  B-63391/90  11/1993

(Continued)

OTHER PUBLICATIONS

PCT International Search Report, mailed Aug. 29, 2000 (International Application No. PCT/US00/15065).

(Continued)

*Primary Examiner*—Jill Warden
*Assistant Examiner*—Jyoti Nagpaul
(74) *Attorney, Agent, or Firm*—Cook Alex Ltd.

(57) ABSTRACT

Apparatus, systems and methods are disclosed for treating a biological fluid with light. A container of biological fluid is introduced into a fluid treatment chamber where it is contacted with light provided by one or more light sources in proximity to the fluid treatment chamber. A drawer for holding containers of biological fluid introduces the containers into the chamber. Containers for holding the biological fluid are marked by the apparatus to indicate the status of the treatment.

8 Claims, 25 Drawing Sheets

U.S. PATENT DOCUMENTS

| | | |
|---|---|---|
| 3,707,806 A | 1/1973 | Toews et al. |
| 3,870,042 A | 3/1975 | Viguier |
| 3,966,286 A | 6/1976 | Groseclose |
| 3,986,506 A | 10/1976 | Garber et al. |
| 4,035,304 A | 7/1977 | Watanabe |
| 4,066,556 A | 1/1978 | Vaillancourt |
| 4,073,723 A | 2/1978 | Swank et al. |
| 4,092,246 A | 5/1978 | Kummer |
| 4,162,676 A | 7/1979 | Talcott |
| 4,223,675 A | 9/1980 | Williams |
| 4,235,233 A | 11/1980 | Mouwen |
| 4,294,247 A | 10/1981 | Carter |
| 4,396,383 A | 8/1983 | Hart |
| 4,437,472 A | 3/1984 | Naftulin |
| 4,458,733 A | 7/1984 | Lyons |
| 4,484,920 A | 11/1984 | Kaufman et al. |
| 4,507,114 A | 3/1985 | Bohman et al. |
| 4,568,328 A | 2/1986 | King |
| 4,573,960 A | 3/1986 | Goss |
| 4,573,961 A | 3/1986 | King |
| 4,573,962 A | 3/1986 | Troutner |
| 4,578,056 A | 3/1986 | King et al. |
| 4,596,547 A | 6/1986 | Troutner |
| 4,608,255 A | 8/1986 | Kahn et al. |
| 4,623,328 A | 11/1986 | Hartranft |
| 4,670,013 A | 6/1987 | Barnes et al. |
| 4,726,949 A | 2/1988 | Miripol et al. |
| 4,776,455 A | 10/1988 | Anderson et al. |
| 4,786,286 A | 11/1988 | Cerny et al. |
| 4,834,743 A | 5/1989 | Valerio |
| 4,866,282 A | 9/1989 | Miripol et al. |
| 4,880,425 A | 11/1989 | Kuhlemann et al. |
| 4,900,321 A | 2/1990 | Kaufman et al. |
| 4,921,473 A | 5/1990 | Lee et al. |
| 4,938,758 A | 7/1990 | Al-Siofi |
| 4,952,812 A | 8/1990 | Miripol et al. |
| 4,976,707 A | 12/1990 | Bodicky et al. |
| 4,976,851 A | 12/1990 | Tanokura et al. |
| 4,997,083 A | 3/1991 | Loretti et al. |
| 5,024,536 A | 6/1991 | Hill |
| 5,030,200 A | 7/1991 | Judy et al. |
| 5,049,146 A | 9/1991 | Bringham et al. |
| 5,080,747 A | 1/1992 | Veix |
| 5,087,636 A | 2/1992 | Jamieson et al. |
| 5,089,146 A | 2/1992 | Carmen et al. |
| 5,098,371 A | 3/1992 | Juji et al. |
| 5,100,401 A | 3/1992 | Patel |
| 5,128,048 A | 7/1992 | Stewart et al. |
| 5,154,716 A | 10/1992 | Bauman et al. |
| 5,176,634 A | 1/1993 | Smith et al. |
| 5,180,504 A | 1/1993 | Johnson et al. |
| 5,184,020 A | 2/1993 | Hearst et al. |
| 5,217,627 A | 6/1993 | Pall et al. |
| 5,269,946 A | 12/1993 | Goldhaber et al. |
| 5,290,221 A | 3/1994 | Wolf, Jr. et al. |
| 5,298,165 A | 3/1994 | Oka et al. |
| 5,300,019 A | 4/1994 | Bischof et al. |
| 5,330,462 A | 7/1994 | Nakamura |
| 5,354,262 A | 10/1994 | Boehringer et al. |
| 5,373,966 A | 12/1994 | O'Reilly et al. |
| 5,403,304 A | 4/1995 | Ishida |
| 5,405,343 A | 4/1995 | Mohr |
| 5,417,681 A | 5/1995 | Miyake et al. |
| 5,427,695 A | 6/1995 | Brown |
| 5,445,629 A | 8/1995 | Debrauwere et al. |
| 5,459,030 A | 10/1995 | Lin et al. |
| 5,462,526 A | 10/1995 | Barney et al. |
| 5,468,373 A | 11/1995 | Chou |
| 5,472,621 A | 12/1995 | Matkovich et al. |
| 5,503,721 A | 4/1996 | Hearst et al. |
| 5,507,525 A | 4/1996 | Leuenberger |
| 5,514,106 A | 5/1996 | D'Silva |
| 5,523,004 A | 6/1996 | Tanokura et al. |
| 5,527,704 A | 6/1996 | Wolf, Jr. et al. |
| 5,536,238 A | 7/1996 | Bischof |
| 5,543,062 A | 8/1996 | Nishimura |
| 5,545,516 A | 8/1996 | Wagner |
| 5,557,098 A | 9/1996 | D'Silva |
| 5,560,403 A | 10/1996 | Balteau et al. |
| 5,562,836 A | 10/1996 | Joie et al. |
| 5,571,666 A | 11/1996 | Floyd et al. |
| 5,573,527 A | 11/1996 | Macabasco et al. |
| 5,593,823 A | 1/1997 | Wollowitz et al. |
| 5,601,730 A | 2/1997 | Page et al. |
| 5,606,169 A | 2/1997 | Hiller et al. |
| 5,627,426 A | 5/1997 | Whitman et al. |
| 5,637,451 A | 6/1997 | Ben-Hur et al. |
| 5,658,722 A | 8/1997 | Margolis-Nunno et al. |
| 5,660,731 A | 8/1997 | Piechocki et al. |
| 5,683,661 A | 11/1997 | Hearst et al. |
| 5,691,132 A | 11/1997 | Wollowitz et al. |
| 5,695,489 A | 12/1997 | Japuntich |
| 5,709,991 A | 1/1998 | Lin et al. |
| 5,724,988 A | 3/1998 | Dennehey et al. |
| RE35,804 E | 5/1998 | Stewart |
| 5,772,644 A | 6/1998 | Bark et al. |
| 5,772,880 A | 6/1998 | Lynn et al. |
| 5,785,700 A | 7/1998 | Olson |
| 5,789,150 A | 8/1998 | Margolis-Nunno et al. |
| 5,792,133 A | 8/1998 | Rochat |
| 5,824,216 A | 10/1998 | Joie et al. |
| 5,836,934 A | 11/1998 | Beshel |
| 5,843,049 A | 12/1998 | Heilmann et al. |
| 5,858,015 A | 1/1999 | Fini |
| 5,858,641 A | 1/1999 | Shanbrom |
| 5,910,138 A | 6/1999 | Sperko et al. |
| 5,922,278 A | 7/1999 | Champman et al. |
| 5,928,213 A | 7/1999 | Barney et al. |
| 5,935,092 A | 8/1999 | Sun et al. |
| 5,951,509 A | 9/1999 | Morris |
| 5,954,527 A | 9/1999 | Jhuboo et al. |
| 6,190,609 B1 | 2/2001 | Chapman et al. |
| 6,190,855 B1 | 2/2001 | Herman et al. |
| 6,245,570 B1 | 6/2001 | Grimm et al. |
| 6,565,802 B1 | 5/2003 | Hanley et al. |
| 2003/0035751 A1 | 2/2003 | Hanley et al. |

FOREIGN PATENT DOCUMENTS

| | | |
|---|---|---|
| EP | 0196515 A1 | 8/1986 |
| EP | 0491757 B1 | 8/1990 |
| EP | 0526678 A1 | 10/1993 |
| EP | 00 93 9469 | 7/2002 |
| WO | WO 92/19284 | 4/1992 |
| WO | WO 92/11057 | 7/1992 |
| WO | WO 96/40857 | 12/1996 |
| WO | WO 98/28057 | 12/1997 |
| WO | WO 98/30327 | 7/1998 |

OTHER PUBLICATIONS

Matthews, et al., "Photodynamic therapy of viral contaminants with potential for blood banking applications," *Transfusion* 28: 81-83 (1988).

Rawal, et al., "Reduction of human immunodeficiency virus-infected cells from donor blood by leukocyte filtration," *Transfusion*, vol. 29, No. 5, 460-462 (1989).

Judy, "Photodynamic action of viruses and in potential application for blood banking," *Newsletter of the Midwest Bio-Laser Institute*, pp. 1-6 (1989).

Bruisten, et al., "Efficiency of white cell filtration and a freeze-thaw procedure for removal of HIV-infected cells from blood," *Transfusion* 30: 833-837 (1990).

Rawal, et al., "Dual reduction in the immunologic and infectious complications of transfusion by filtration/removal of leukocytes from donor blood soon after collection," *Transfusion Medicine Reviews*, pp. 36-41 (1990).

Taylor, et al., "Human T-cell lymphotropic virus in volunteer blood donor," *Transfusion*, vol. 30, No. 9 (1990)

Wagner, et al., "Approaches to the reduction of viral infectivity in cellular blood components and single donor plasma," *Transfusion Medicine Reviews*, vol. V, No. 1, 18-32 (Jan. 1991).

Sadoff, et al., "Experimental 6 log10 white cell-reduction filters for red cells," *Transfusion*, 32: 129-133 (1992).

Eisenfeld, et al., "Prevention of transfusion-associated cytomegalovirus infection in neonatal patients by the removal of white cells from blood," *Transfusion* 32: 205-209 (1992).

Tuite, et al., "Photochemical interactions of methylene blue and analogues with DNA and other biological substrates," *J. Photochem., Photobiol. B. Biol.*, 21, pp. 103-124 (1993).

Ben-Hur, et al., "Inhibition of phthalocyanine-sensitized photochemolysis of human erythrocytes by quercetin," *Photochemistry and Photobiology*, vol. 57, No. 6, 984-988 (1993).

Ben-Hur, et al., "Virus inactivation in red cell concentrates by photosensitization with pthalocyanines: Protection of red cells but not of vesicular stomatitis virus with a water-soluble analogue of vitamin E," *Transfusion*, vol 35, No. 5 (1995).

Rywkin, et al., "New phthalocyanines for photodynamic virus inactivation in red blood cell concentrates," *Photochemistry and Photobiology*, vol. 60, No. 2, 165-170 (1994).

Rywkin, et al., "Selective protection against IgG binding to red cells treated with phthalocyanines and red light for virus inactivation," *Transfusion*, vol. 35, No. 5 (1995).

Margolis-Nunno, et al., "Elimination of potential mutagenicity in platelet concentrates that are virally inactivated with psoralens and ultraviolet A light," *Transfusion*, 35: 855-862 (1995).

Wagner, et al., "Factors affecting virus photoinactivation by a series of phenonthiazine dyes," *Photochemistry and Photobiology*, 67(3): 343-349 (1998).

Ben-Hur, et al., "Photodynamic decontamination of blood for transfusion," New York Blood Center, 310 E. 67th Street, New York, NY 10021.

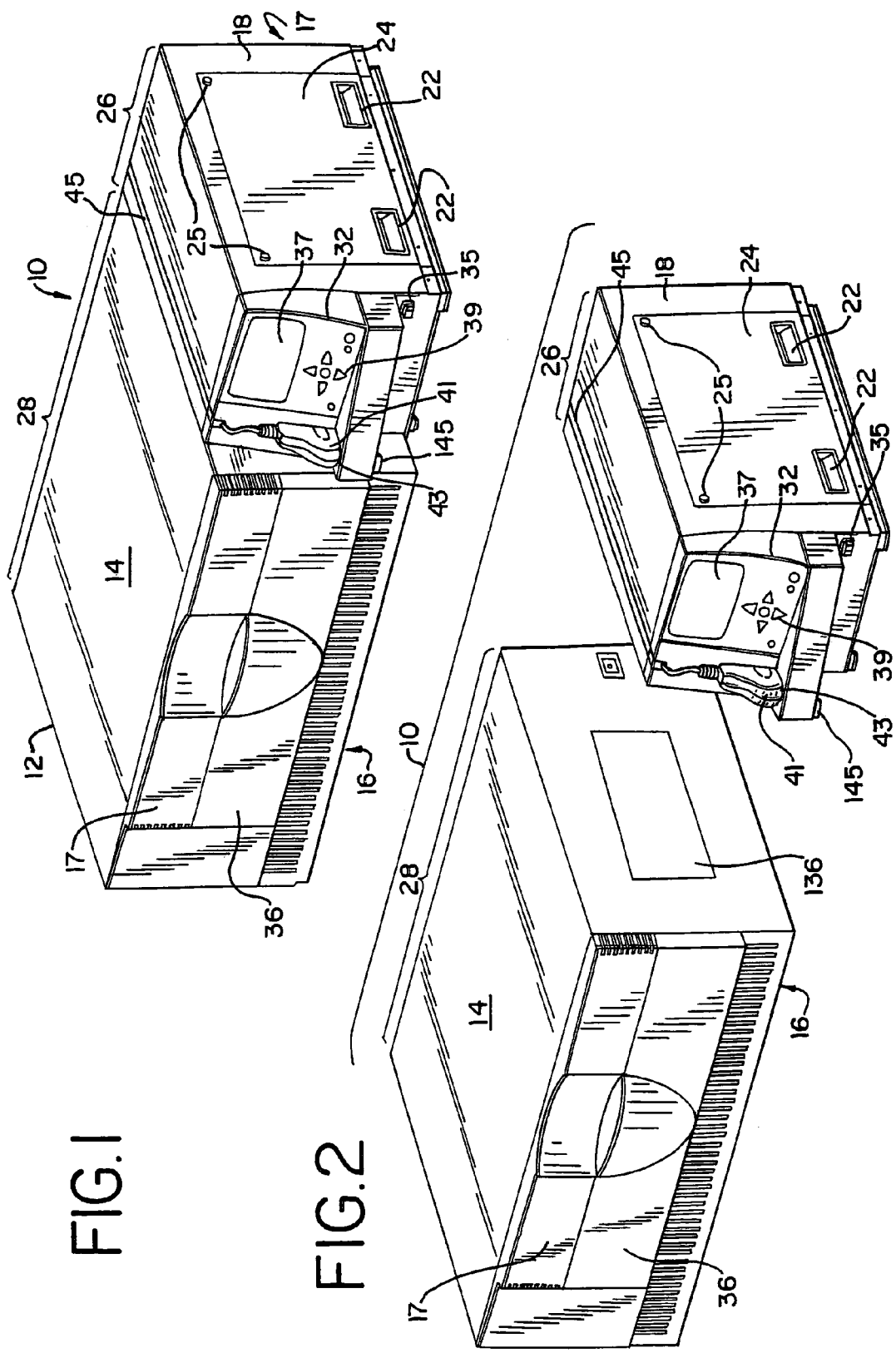

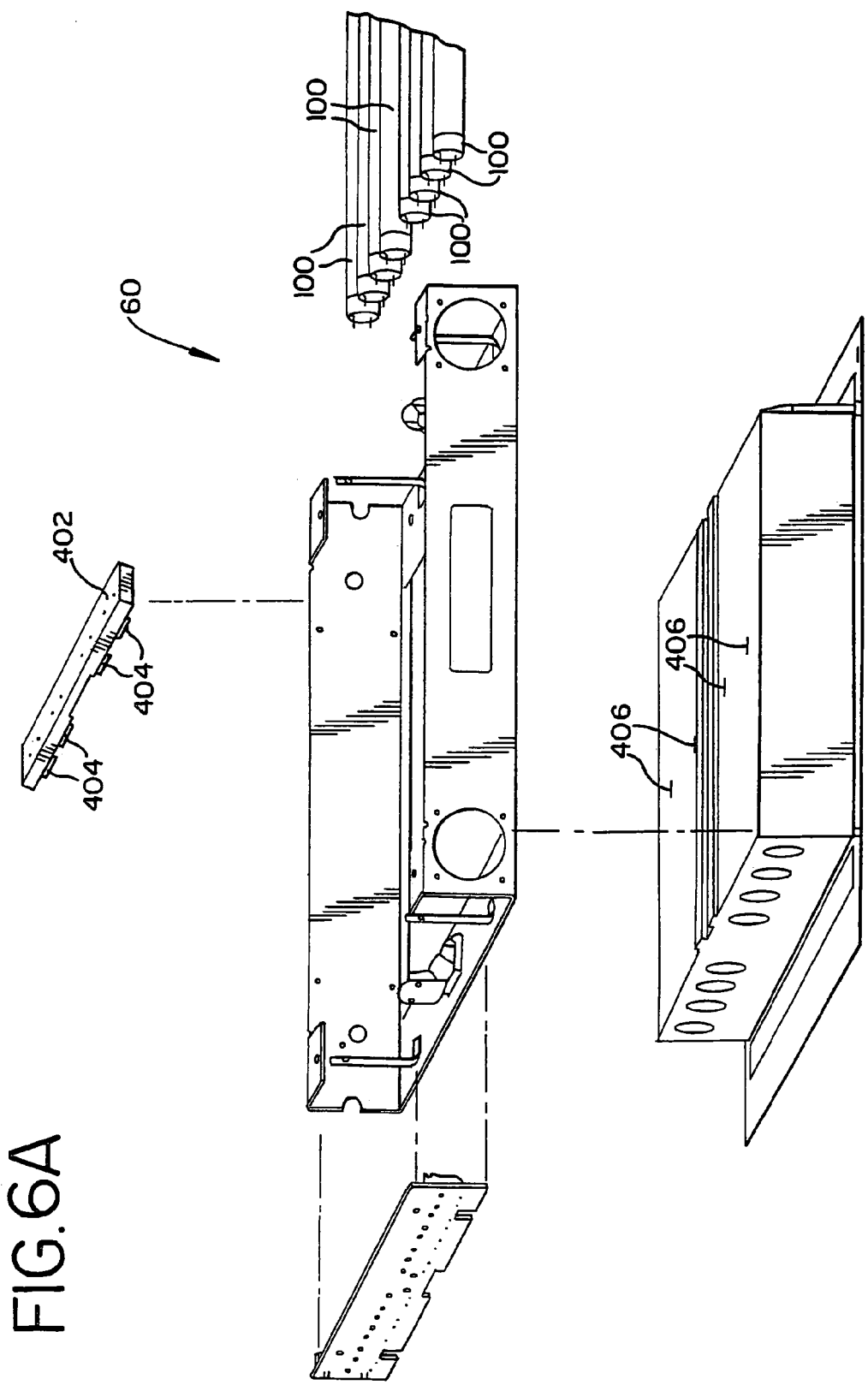

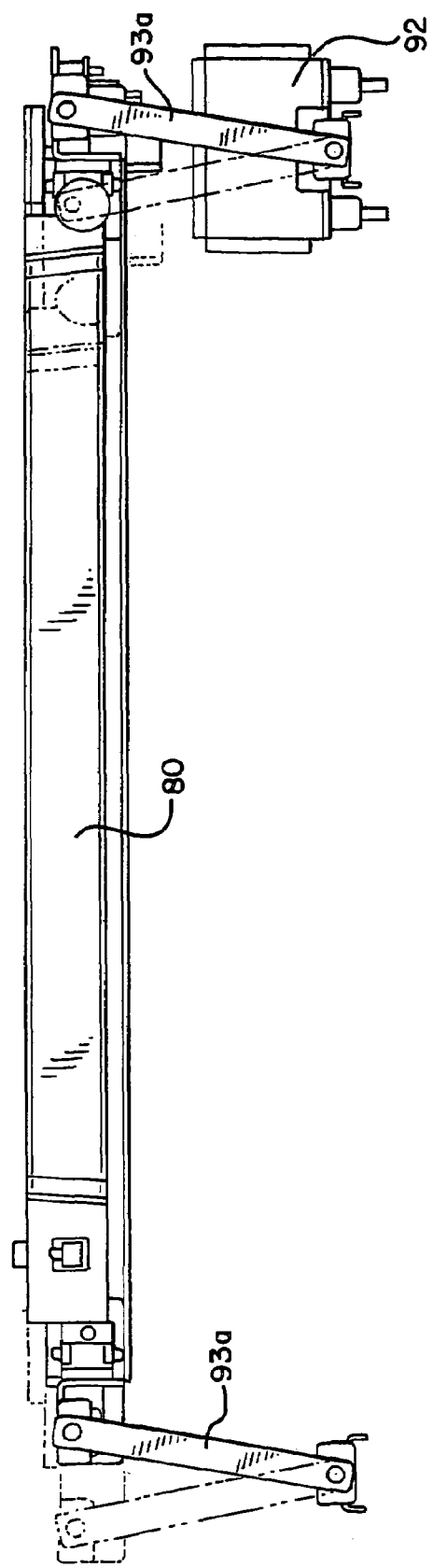

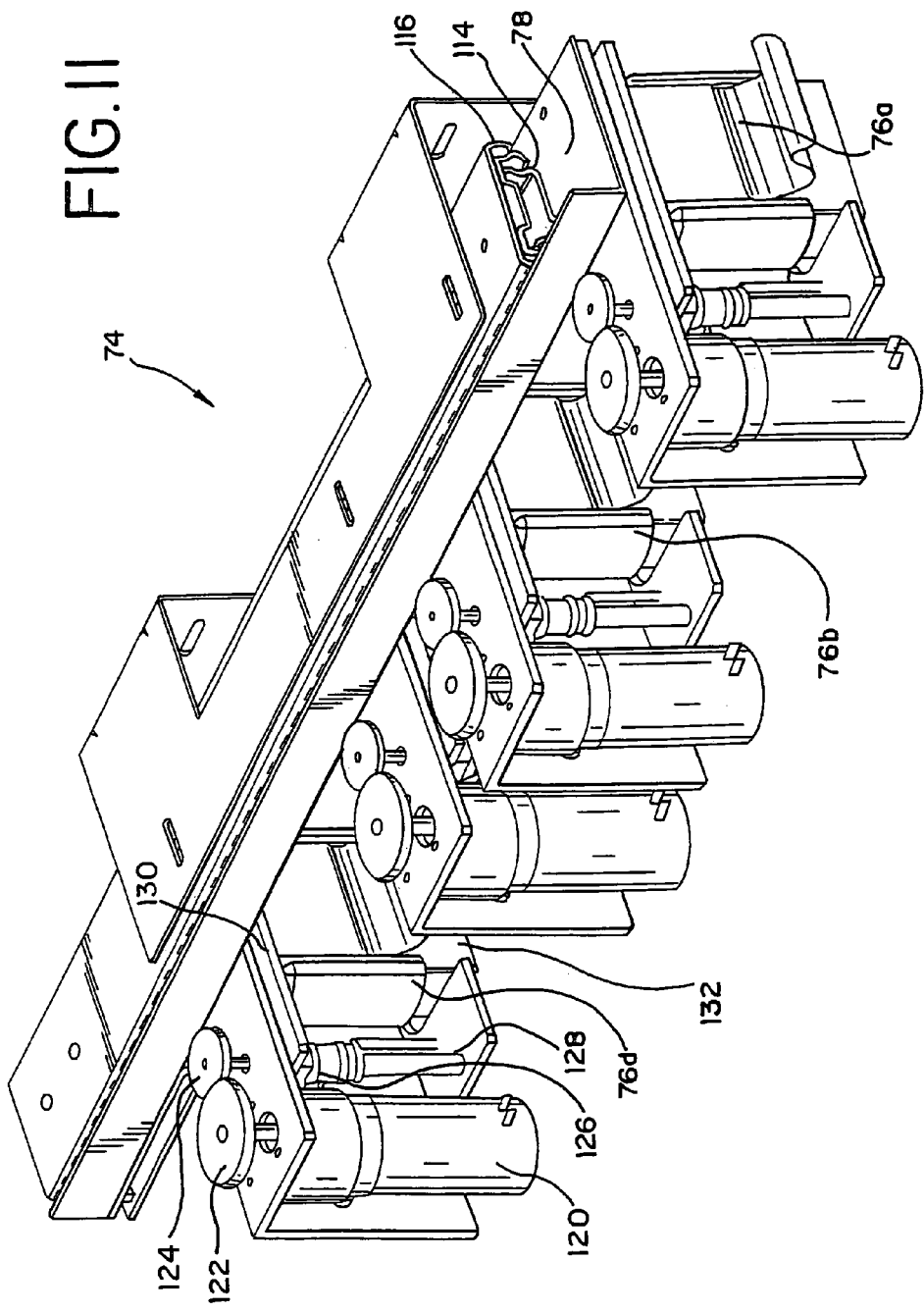

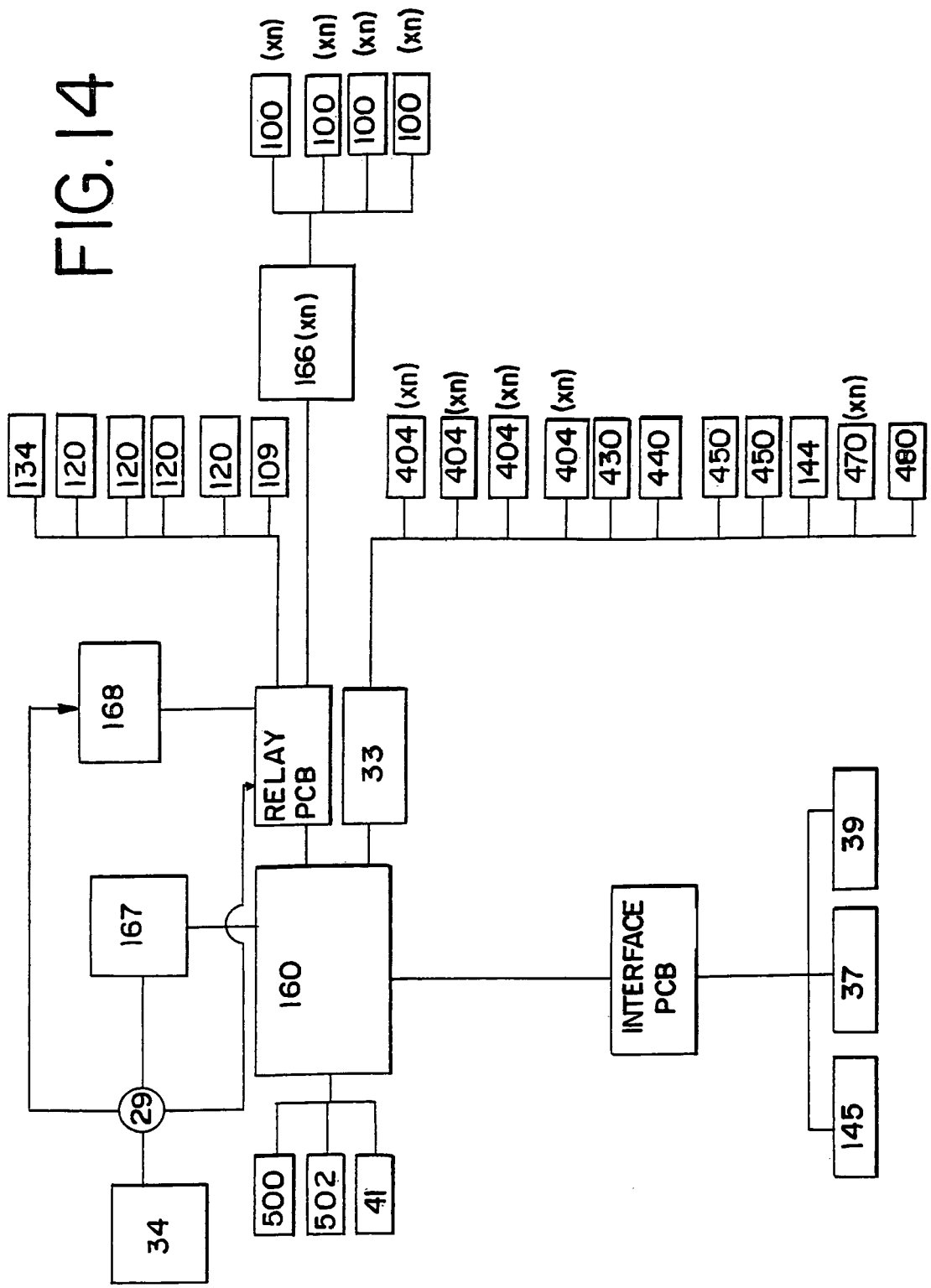

FIG. 17
FIG. 18
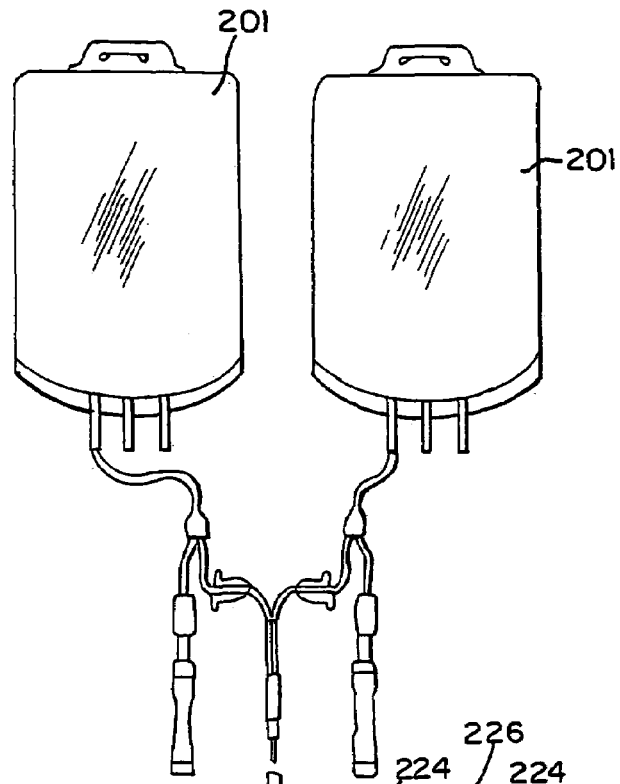
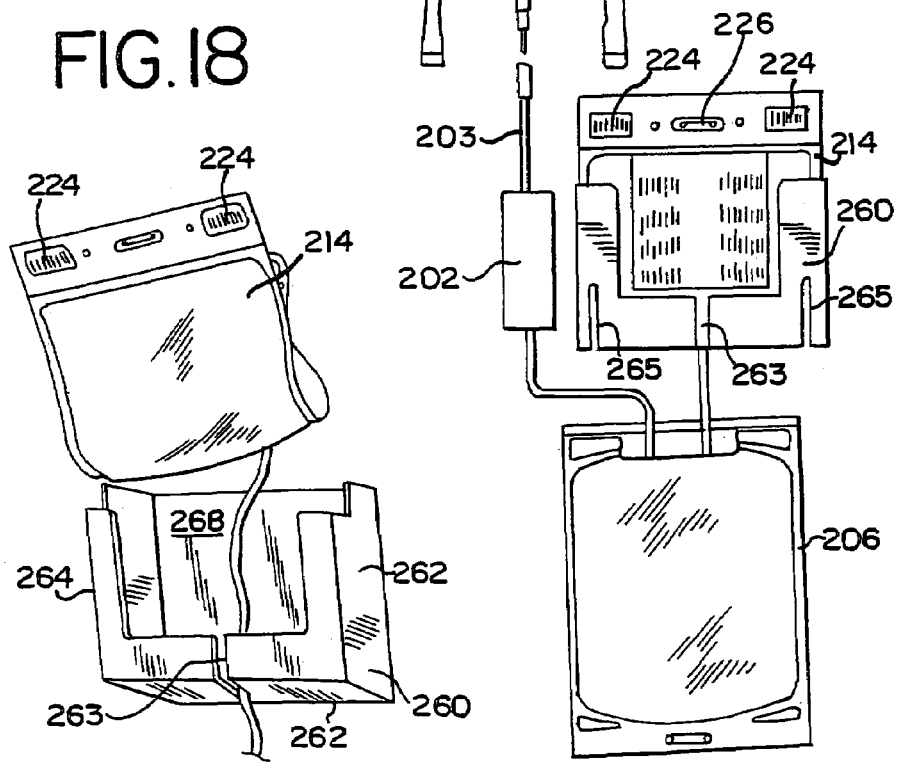

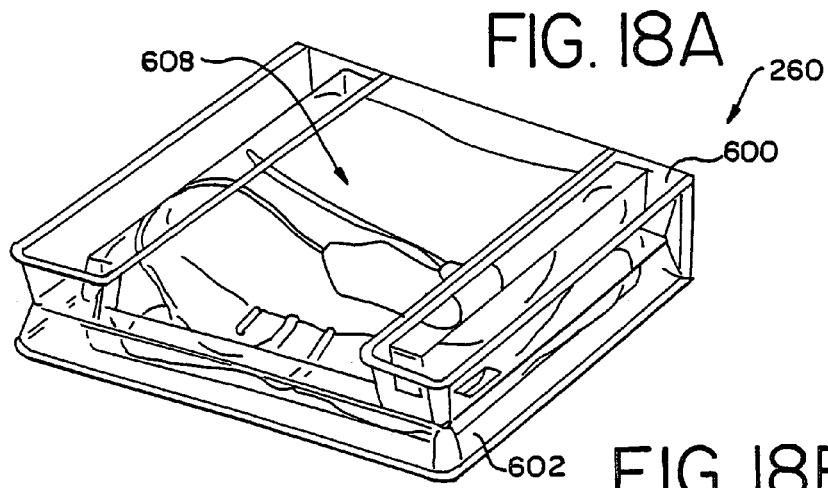
FIG. 18A
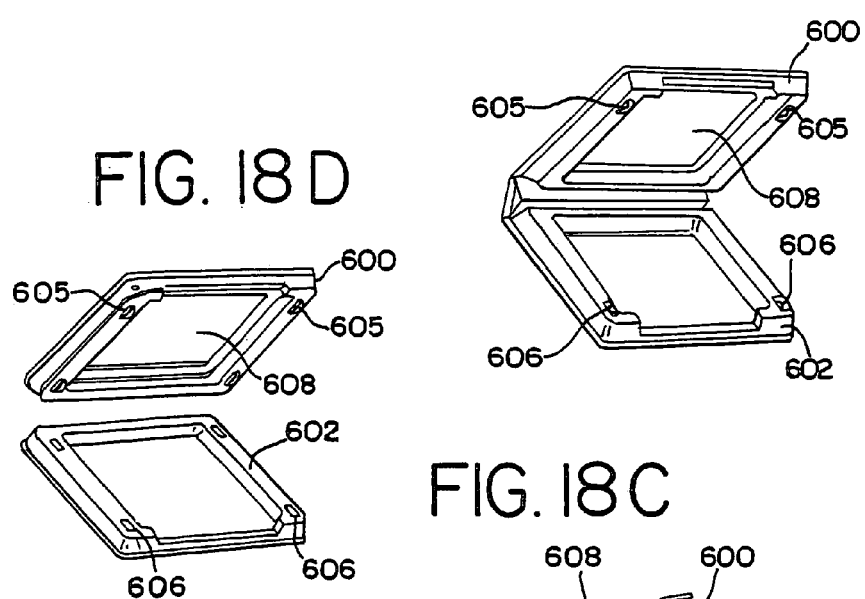
FIG. 18B
FIG. 18D
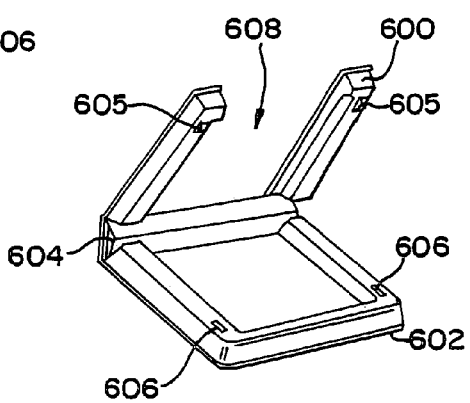
FIG. 18C

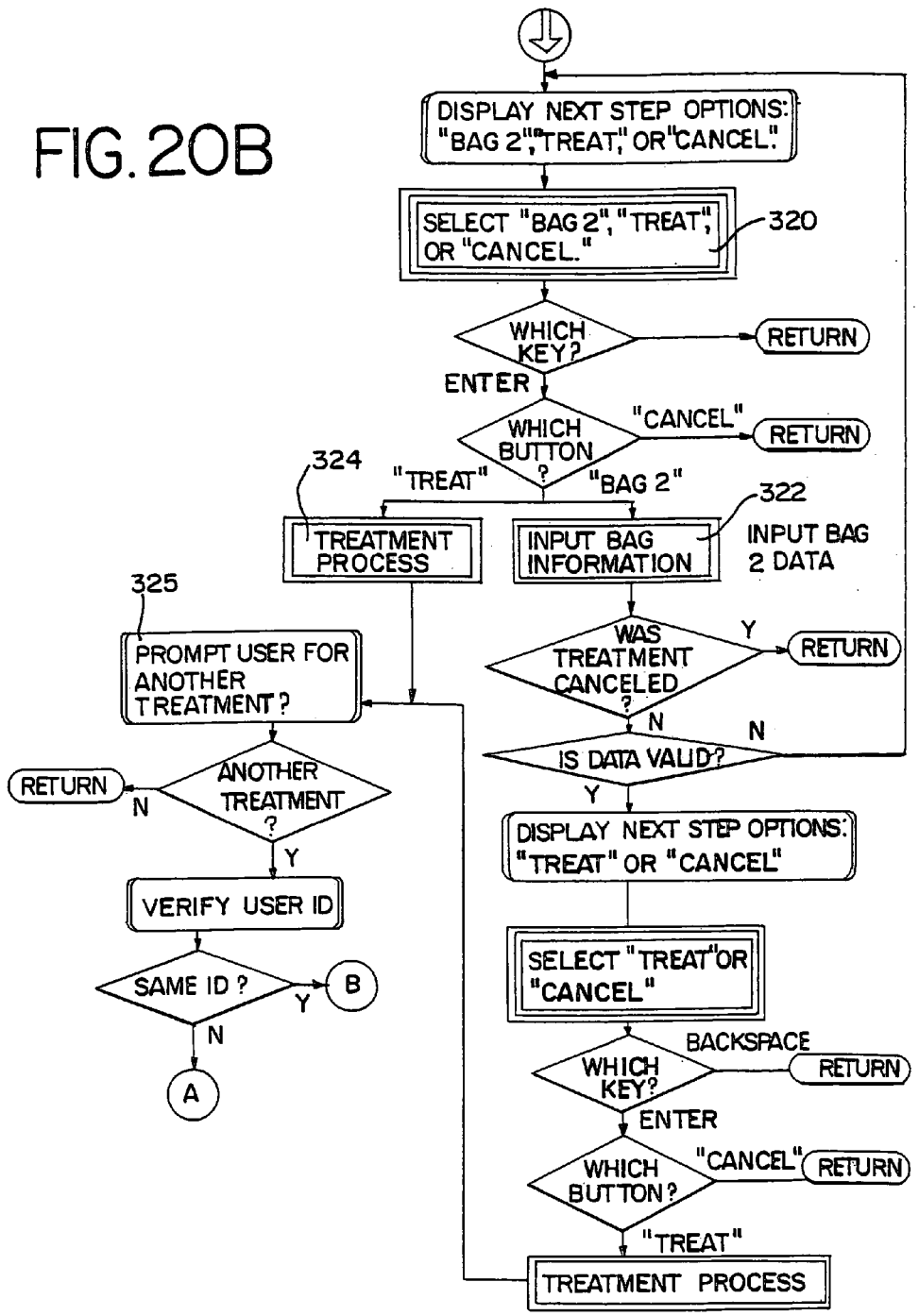

PROCESSING SET AND METHODS FOR PROCESSING AND TREATING A BIOLOGICAL FLUID

This is a divisional application of U.S. patent application Ser. No. 09/325,599, now U.S. Pat. No. 7,025,877, filed Jun. 3, 1999, which is incorporated by reference.

The present invention generally relates to apparatus, systems and methods for processing and treating biological fluids, such as blood and blood components. More particularly, the present invention relates to improved apparatus, systems and methods for the light treatment of a biological fluid that contains a light activated photochemical agent, for the purpose of inactivating pathogens that may be present in such biological fluid.

Apparatus, methods and systems for treating biological fluids, such as blood and blood components, with light are well known. For example, U.S. Pat. No. 4,952,812, incorporated by reference herein, discloses an apparatus for treating unwanted white blood cells in platelet concentrate with ultraviolet radiation to limit the white cells' ability to trigger an immune reaction in a patient. To treat containers of platelet concentrate, the containers are placed on a slidable drawer that is introduced into a housing between facing arrays of lamps for irradiation from both sides of the container. During irradiation, the drawer (or a portion of the drawer) may be pivoted in a rocking motion to agitate the platelet concentrate.

U.S. Pat. No. 5,557,098, also incorporated by reference herein, discloses a system and apparatus for treating a biological fluid with light for the purpose of inactivating pathogens that may be present in the biological fluid. A slidable drawer is used to position the containers of biological fluid between facing arrays of light emitting diodes. Extended flaps on the containers, located outside the light field, are automatically punched to indicate different stages of the light treatment.

U.S. patent application Ser. No. 08/121,820, filed Sep. 15, 1993, which is also incorporated by reference herein, discloses apparatus and methods for treating a container of a blood product between two facing arrays of light. The container includes a light sensitive tape which changes color when exposed to ultraviolet light, thereby indicating when the treatment process is complete.

Still other apparatus and systems for treating biological fluid are disclosed in U.S. Pat. No. 5,709,991, and U.S. patent application Ser. No. 09/081,168, filed May 18, 1998, both of which are incorporated by reference herein.

While the prior art apparatus, systems and methods have generally worked satisfactorily, work continues to develop new and improved apparatus, systems and methods that provide, for example, improved reliability, greater flexibility and efficiency, improved ease of use and serviceability, as well as enhanced tracking, record keeping and the like.

SUMMARY OF THE INVENTION

In accordance with one aspect of the subject matter of the application, a pre-assembled disposable fluid processing set for use in a photoactivation treatment of a biological fluid is provided. The disposable fluid processing set preferably includes a first container containing a photochemical agent and being adapted for joinder to a source container of biological fluid. The first container is preferably enclosed within an overwrap that is impermeable to light of a selected photoactivating wavelength range. The disposable fluid processing set also preferably includes a second container downstream of and pre-attached to the first container for holding the biological fluid and the photochemical agent during a photoactivation treatment, and is preferably made of a material that is substantially translucent to light in the photoactivating wavelength range. There is a sealed but openable flow path between the first and second containers. The fluid processing set includes a flow-through device downstream of and pre-attached to the second container for receiving at least the biological fluid from the second container. The device includes adsorbent material for removing at least one or both of excess photochemical agent and photoactivation by-products from the biological fluid. There is a sealed but openable flow path between the second container and the flow-through device. The fluid processing set further includes a container downstream of and pre-attached to the device for receiving biological fluid from the device.

BRIEF DESCRIPTION OF THE DRAWINGS

FIG. 1 is a perspective view of an apparatus for treating a biological fluid with light, embodying the present invention;

FIG. 2 is a perspective view of the apparatus of FIG. 1 showing the modular components of the apparatus separated;

FIG. 6A is an exploded view of the light drawer of FIG. 6.

FIG. 10 is a front view of the fluid carrying drawer with fluid carrying tray removed showing side to side oscillation of the tray;

FIG. 11 is a perspective view of container marker assembly;

FIG. 14 is a block diagram of the control system of the apparatus embodying the present invention;

FIG. 17 is a plan view of a disposable fluid processing set embodying the present invention in position for attachment with containers of a collected biological fluid;

FIG. 18 is a perspective view of a part of the disposable fluid processing set embodying the present invention that includes at least one container disposed within a holder;

FIG. 18A is a perspective view of an alternative embodiment of the holder in a closed position with containers disposed therein;

FIG. 18B is a perspective view of the holder of FIG. 18A in an open position but without container(s);

FIG. 18C is a perspective view of another alternative embodiment of a holder in an open position;

FIG. 18D is a perspective view of another alternative embodiment of a holder with frame portions separated;

FIG. 20B is a continuation of the flow chart of FIG. 20A;

DETAILED DESCRIPTION

For purposes of illustration, the various aspects of the present invention will be described, in large part, in connection with their preferred embodiments. However, it should be recognized that the apparatus, systems and methods embodying the different aspects of the present invention are not limited to the specific details described herein.

An apparatus for treating a biological fluid is generally shown in FIGS. 1-14 and is referred to herein generally as light box 10. Light box 10 may be used for treating a variety of materials for a variety of purposes.

Light box 10 is particularly useful in the treatment of biological fluids. As used herein, biological fluid refers to any fluid that is found in or that may be introduced into the body including, but not limited to, blood and blood products. As used herein "blood product" refers to whole blood or a component of whole blood such as red blood cells, white blood cells, platelets, plasma or a combination of one or more of such components that have been separated from whole blood.

One specific, non-limiting use of light box 10 is in the treatment of a blood product that has been combined with a photochemical agent for activation when subjected to light. Such photochemical agents are used, for example, in the inactivation of viruses, bacteria, white blood cells and other contaminants (collectively referred to herein as "pathogens"). In pathogen inactivation applications, the activated agent inactivates pathogens that may be present in a blood product.

Typically, the biological fluid to be treated is introduced into a fluid treatment chamber within light box 10 in flexible, plastic, sterilizable, translucent, biologically compatible containers. In accordance with aspects of the present invention, the containers may be integrally connected to other containers and plastic tubing useful in the processing of the biological fluid both before and after the treatment provided by light box 10. Examples of the disposable processing set and its components are shown in FIGS. 15-18. The light box, the disposable processing set and the methods of using them are described in more detail below.

a. Light Box

Figure 4:
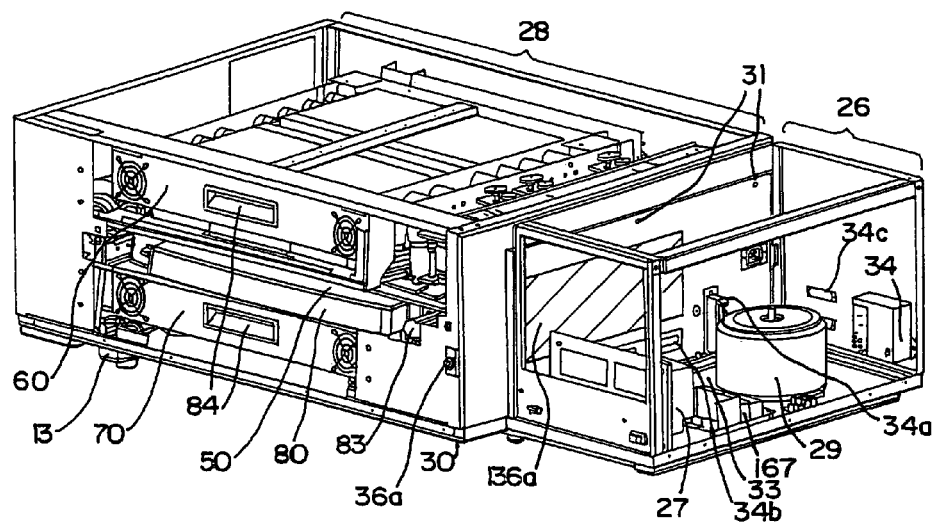
FIG. 4 is a perspective view of the apparatus of FIG. 1 with front, top and side panels removed.

As shown in FIG. 1, light box 10 includes a housing 12 defined by top panel 14, bottom panel 16, front and rear panels 17, and side panels 18. Housing 12 is supported by feet 13 attached to bottom panel 16 (FIG. 4). In a preferred embodiment, feet 13 are rubber or other elastomeric mounts. Side panels 18 may include handles 22 for grasping and transporting light box 10. An openable or removable door 24 in side panel 18 allows for access to the interior of light box 10 and, more specifically, the electronic components of light box 10, which are described in more detail below. Door 24 may be opened or removed by turning fasteners 25.

Figure 13:
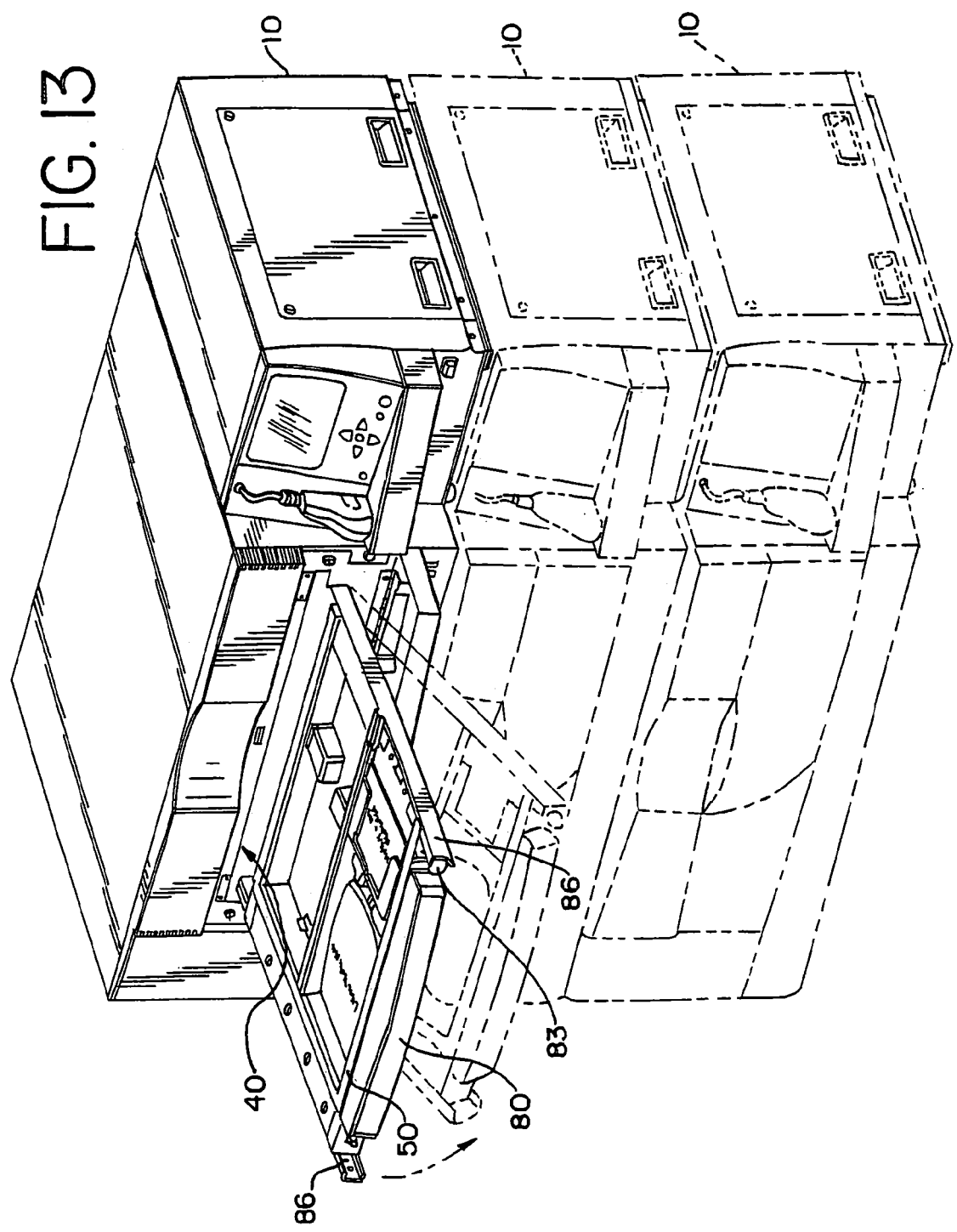
FIG. 13 is a perspective view of stacked apparatus embodying the present invention.

For convenience and efficiency, it is preferred that light box 10 be fairly compact. In one, non-limiting example, light box 10 may be approximately 100 cm wide, 20-40 cm deep and between approximately 30-40 cm high. A compact instrument allows, for example, for placement of a greater number of instruments per treatment center and/or may allow two or more instruments to be stacked on top of each other (as shown in FIG. 13), resulting in greater throughput of biological fluid per horizontal area or space (i.e. bench space, shelf space).

Light box 10 may include a control module 26 and a fluid treatment module 28. As described in more detail below, control module 26 may include and/or house the command and control elements for the treatment of biological fluid. Fluid treatment module 28 houses the elements and components where fluid processing takes place.

Control module 26 and fluid treatment module 28 may be contained in the same housing but in a preferred embodiment, as shown in FIG. 2, they are readily separable modules. Control module 26 and fluid treatment module 28 are electrically and physically connected when light box 10 is in use, but may be separated as shown in FIG. 2. In one embodiment, control module 26 and fluid treatment module 28 are held together, in part, by draw pin 30 (FIG. 4) which holds together interfitting parts of the modules. Control module 26 and fluid treatment module 28 may be separated by removing draw pin 30 and turning of fasteners 31 shown in FIG. 4. Fasteners 31 may be accessed by removing door 24 (shown in FIG. 1) in side panel 18. Of course, other means of connecting and readily separating control and fluid treatment modules may be used, including, mating clips and slots on the facing panels of the control 26 and fluid treatment module 28.

Providing light box 10 in two readily separable modules 26 and 28 allows for easier access to the control and fluid treatment modules 26 and 28 and, generally, provides for easier serviceability of light box 10. For example, if off-site service is required for control module 26 only, that module can be removed without requiring removal and transport of the entire light box 10.

As shown in FIGS. 1 and 2, the exterior of control module 26 includes a control panel 32 located in the front of light box 10. Control panel 32 includes, a display screen 37 such as, but not limited to, an LCD display for providing graphical, textual and alphanumerical information to the operator regarding the treatment process. Also included within control panel 32 of control module 26 is a key pad 39 to allow operator control over the process and/or for data entry by the operator. Additional means of data entry are provided by bar code reader 41 which, when not in use, rests in slot 43. A trough 45 may be provided for the coiled cable of bar code reader 41. Control panel may also include the on/off switch 35 for light box 10.

The interior components of control module 26 are generally shown in FIG. 4. Control module 26 will typically include a programmable microprocessor for operation of light box 10 including central processing unit 27 and memory devices such as random access memory (RAM) and EPROMS for the system program storage and non-volatile memory for back-up data storage. Control module 26 may further include an isolation transformer 29 for converting an AC input voltage to a DC control system voltage and for maintaining leakage current within acceptable limits for medical devices. Other components within control module 26 may include power supply 167, input/output board 33 and a power inlet module 34, filtered pass through 34b for use with an external light intensity sensing device and filtered output pass through 34a.

Control module 26 may be adapted for connection to external components such as a printer 500 (FIG. 14) through parallel and/or serial ports 34C, or to a central computer 502 (FIG. 14) that is connected to several light boxes and/or other medical devices. The central computer can receive data from the several instruments, allowing the operator at a treatment center to retrieve information regarding the several procedures. As will be appreciated by one of ordinary skill, control module 26 may also include other components such as additional printed circuit boards shown in FIG. 14

Figure 3:
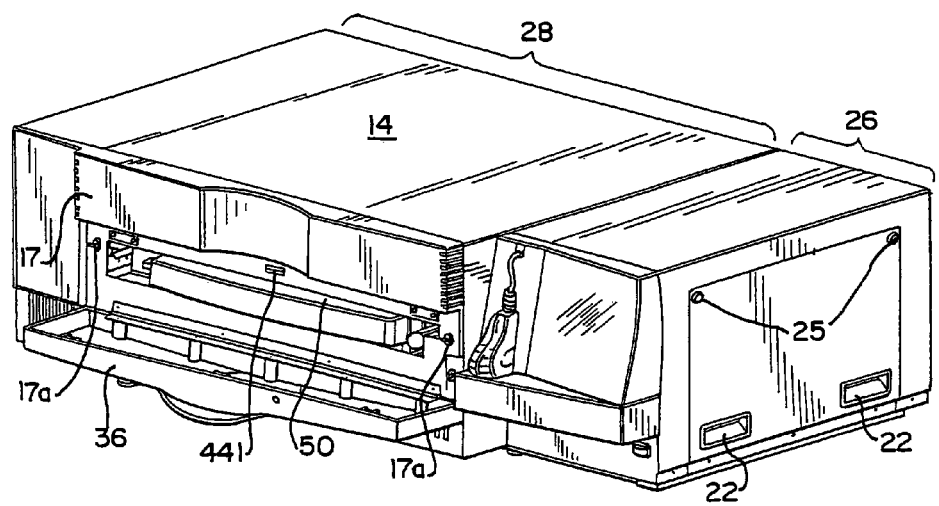
FIG. 3 is a perspective view of the apparatus of FIG. 1 with the front access door open.

Turning now to the fluid treatment module 28, as shown in FIGS. 1-3, fluid treatment module 28 includes front door 36 which when opened, allows for introduction and removal of the biological fluid into a fluid treatment chamber, as described in more detail below. The front panel 17 of fluid treatment module 28 may also be opened to allow for fuller access to the interior of fluid treatment module. As shown in FIG. 3, panel 17 may include fasteners 17a which, when turned, allow front panel 17 to be opened or removed.

Figure 5:
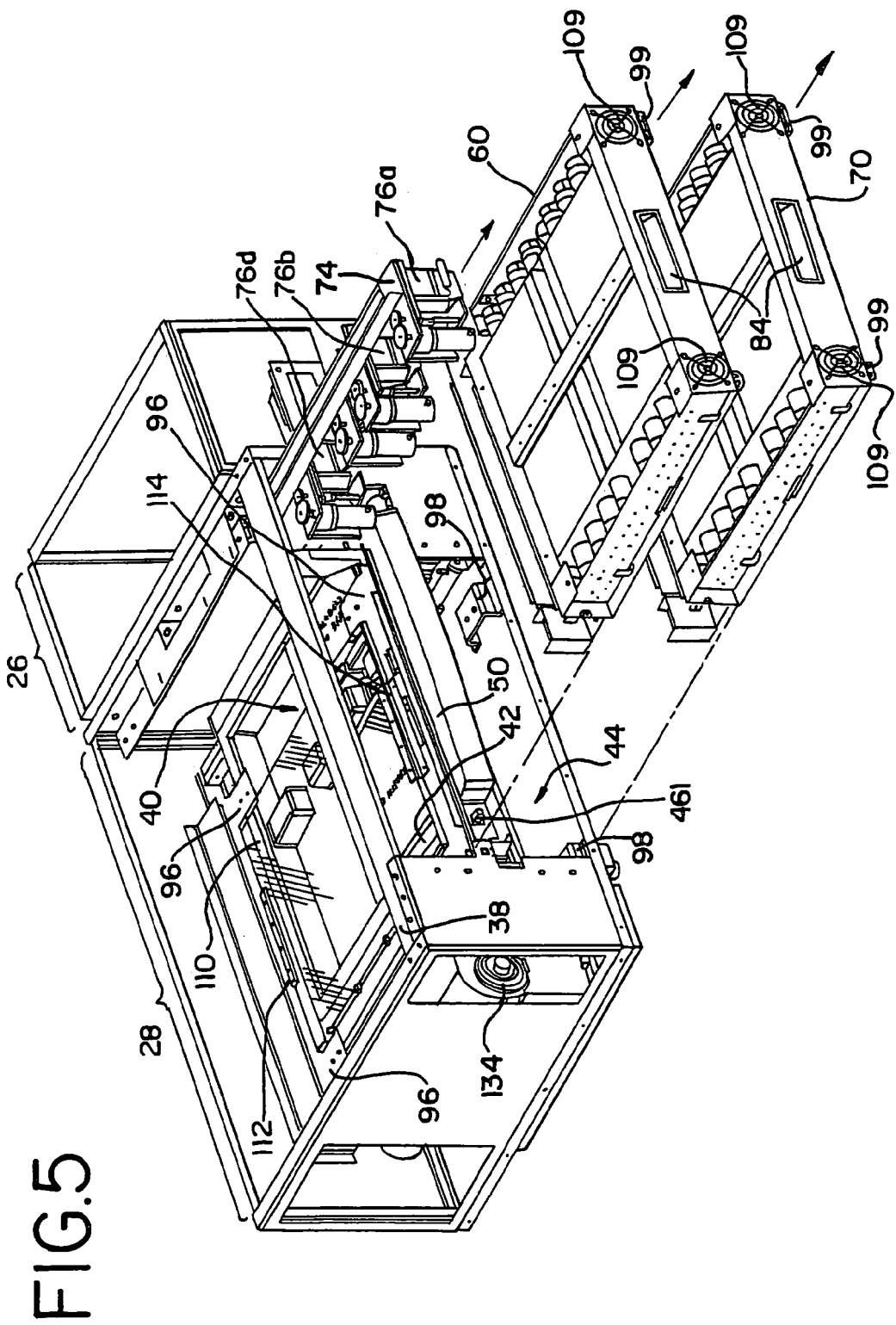
FIG. 5 is a partially exploded view of the apparatus of FIG. 1.

FIGS. 4-5 generally show the interior of fluid treatment module 28 with at least top panel 14 and front panel 17 removed. As best seen in FIG. 5, fluid treatment module 28 includes an interior framework 38 that defines, in part, a fluid treatment chamber 40 and light chambers 42 and 44 for housing light sources (described in more detail below). The framework 38 may typically be constructed of any sturdy material which will allow light box 10 to support one or more additional light boxes as generally shown in FIG. 13. A preferred material is aluminum and, in particular, Aluminum 6061 hardened to T-6.

Returning to FIG. 5, the light chambers 42 and 44 are located above and below fluid treatment chamber 40 to provide two-sided illumination of the biological fluid. Of course, it will be appreciated that light box 10 may include a single light chamber, placed in close proximity to fluid treatment chamber or two or more light chambers disposed around a fluid treatment chamber in other than "top and bottom" positions.

As shown in FIGS. 3-5, fluid treatment chamber 40 is adapted to receive fluid carrying drawer 50. Light chambers 42 and 44 are adapted to receive light drawers 60 and 70. Fluid treatment module 28 may further include a container marker assembly 74 shown, for example, in FIG. 5. Marker assembly 74 may carry one or more markers 76a-76d for marking containers, before and/or after treatment, as will be discussed in more detail below.

Figure 8:
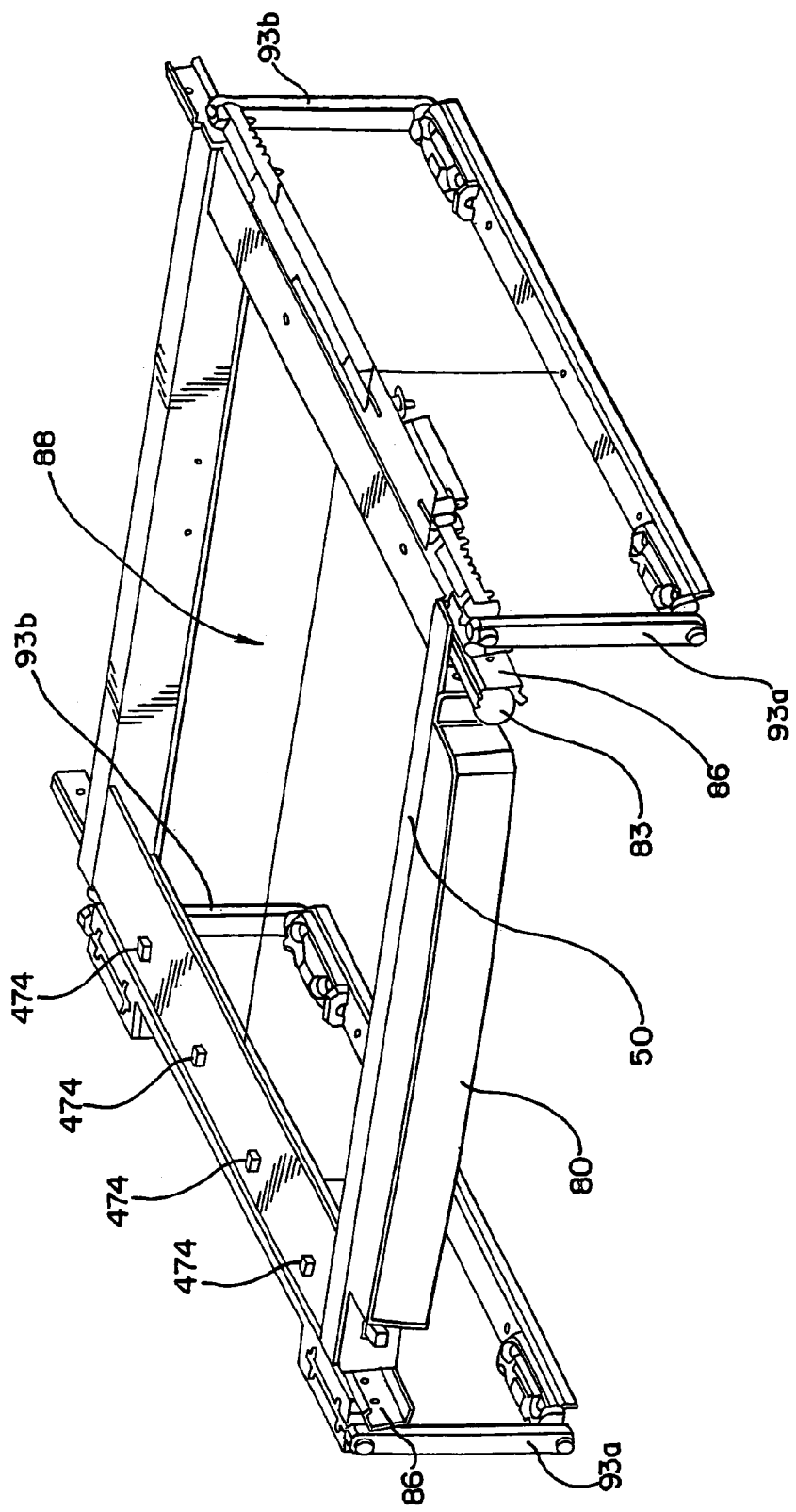
FIG. 8 is a perspective view of fluid carrying drawer with tray removed.
Figure 9:
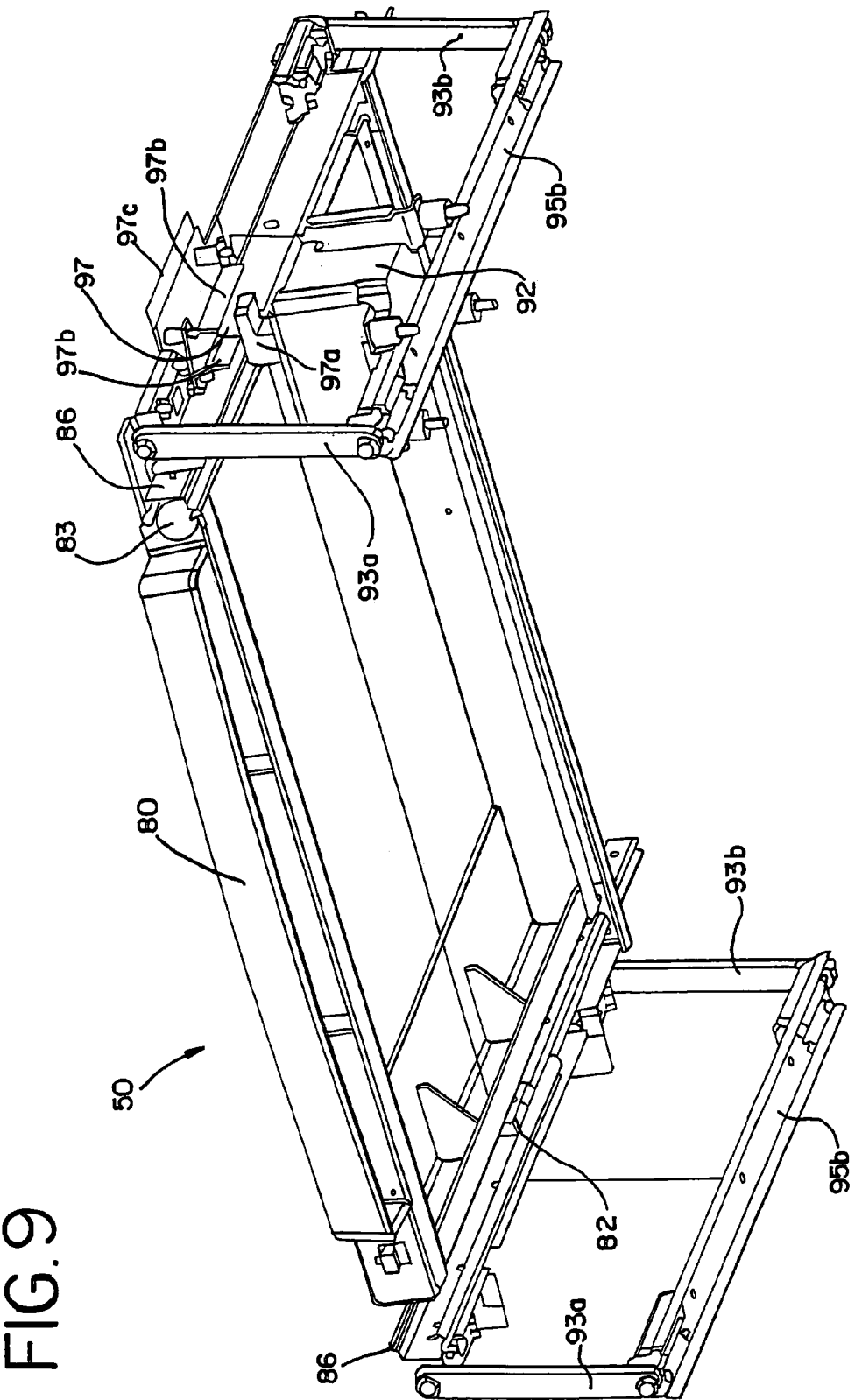
FIG. 9 is another perspective view, from the underside, of the fluid carrying drawer without fluid container carrying tray.

Turning more specifically to a description of fluid carrying drawer 50, as shown in FIG. 13, fluid carrying drawer 50 allows for introduction of biological fluid into fluid treatment chamber 40. Fluid carrying drawer 50 may be moveable, either manually or automatically, into and out of fluid treatment chamber 40. Where manual movement of fluid carrying drawer 50 is required, drawer 40 may include handle 80. In one embodiment, movement of fluid carrying drawer 50 is facilitated by slides 82 on either or both sides of drawer 50, which are disposed within rails 86 of framework 38, as best seen in FIGS. 8, 9 and 13. Alternatively, fluid carrying drawer 50 may include rollers or other devices which allow for movement of drawer 50 into and out of fluid treatment chamber 40.

Figure 8A:
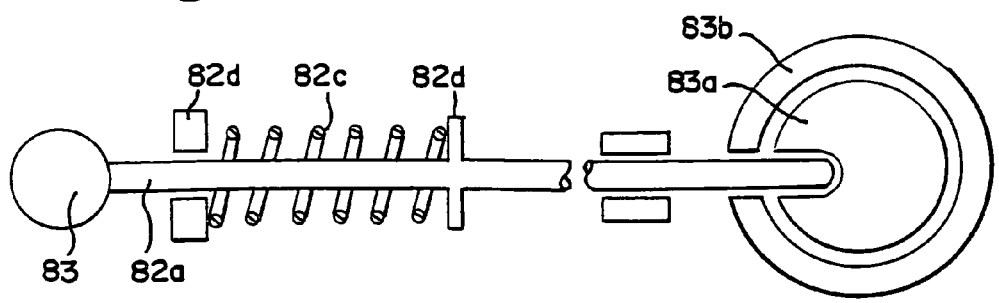
FIG. 8A is a partial side view of the drawer tilt knob and assembly of the fluid carrying drawer.
Figure 8B:
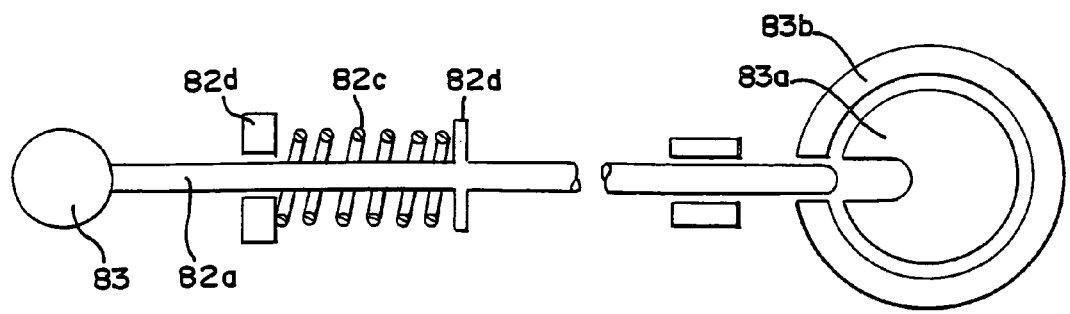
FIG. 8B is a modified partial side view of the drawer tilt knob and assembly of the fluid carrying drawer.

For ease of loading and unloading containers of biological fluid, fluid carrying drawer 50 preferably includes a pivot mount that permits the drawer to be tilted downwardly when fully withdrawn. The ability to tilt drawer 50 downwardly may be particularly useful for loading containers of fluid in the upper light boxes where two or more light boxes are stacked on top of each other, as shown in FIG. 13. In one embodiment, fluid carrying drawer 50 may be hingedly attached to framework 38 so that when fluid carrying drawer 50 is fully opened and is outside of housing 12, front edge of drawer 50 may be tilted downwardly at, for example, a 45° angle. To allow tilting of fluid carrying drawer, light box 10 may include spring loaded tilt knob 83 which, when pulled, releases fluid carrying drawer 50 and allows it to be tilted in the manner described above. More specifically, as shown in FIG. 8A, tilt knob 83 is connected to rod 82a which is attached to slide 82 (FIG. 9). The end of rod 82a is coupled to pivot member 83a which is connected to ring 83b attached to drawer 50. Rod 82a further includes a spring 82c and spring stops 82d. When the end of rod 82a is coupled to pivot member 83a, movement of ring 83b is prevented (as shown in FIG. 8A). However, when knob 83 is pulled, (as shown in FIG. 8B) rod 82a is uncoupled from pivot member 83a, allowing ring to rotate relative to pivot member 83a and, thereby, allowing drawer 50 to be tilted downwardly, as shown in FIG. 13.

Figure 7:
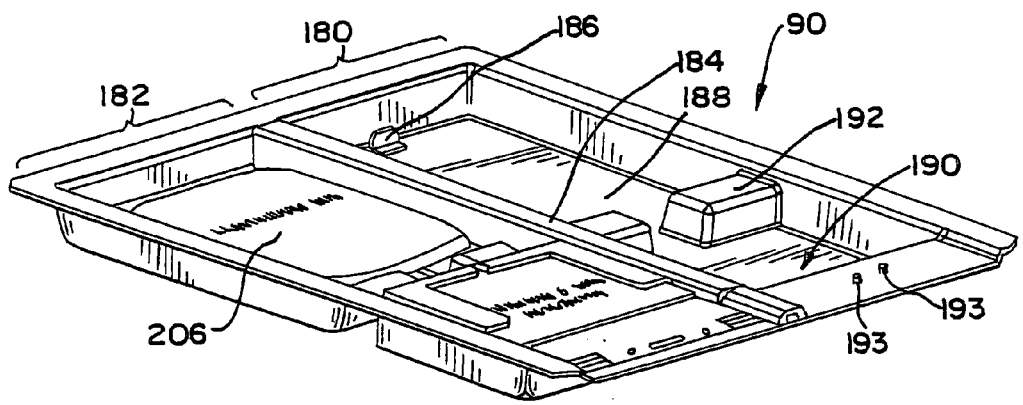
FIG. 7 is a perspective view of a fluid container carrying tray.

As shown in FIGS. 8-9, fluid carrying drawer 50 is generally open and includes a central cavity 88 to allow for placement of a container carrying tray 90 shown in FIG. 7. Container carrying tray 90 may be integral with fluid carrying drawer 50, although, a removable non-integrated tray 90 may be preferable for easier container loading and/or tray cleaning.

During treatment of the biological fluid, it may be desirable that the fluid within fluid carrying drawer 50 be continuously or periodically agitated to provide mixing of the biological fluid and ensure that substantially all of the biological fluid is sufficiently and uniformly exposed to light and/or any photochemical agent. Accordingly, fluid carrying drawer 50 may be attached to means for agitating the biological fluid.

As shown in FIGS. 9 and 10, fluid carrying drawer 50 may include an agitation assembly that, for example, provides side-to side oscillation of tray 90. Agitation assembly may include a pair of fixed lower rails 95b that extend front to back within light chamber. Upper rails 95a are attached to the lower rails by pivotally attached link arms 93a and 93b. The link arms allow side-to-side motion of the upper rails 95a. To provide oscillation, an electrical motor 92 is attached to lower rail 95b. Motor 92 rotates a cam 97a. Cam 97a may be an L-shaped crank or bracket attached to roller 97. Roller 97 is captured between parallel walls 97b depending from upper rail 95a. As crank 97a causes roller 97 to orbit around the motor 92 axis, roller slides fore and aft and up and down between walls 97b, imparting side-to-side motion of upper rail 95a.

Light box 10 may include one or more light sources, preferably disposed above and below fluid treatment chamber 50. For ease of serviceability, such as lamp replacement, it is preferable that the light source(s) be readily accessible. As used herein, "readily accessible" means that access to the light source can be quickly and easily had without the use of, for example, a screwdriver or other tools. For example, in one embodiment, it may be desirable that the light source be either partially or completely removable from the housing 12 and/or fluid treatment module 28. The light source(s) may be accessible through any one of the front, side, top or bottom panels. In one embodiment, the light sources are housed in light drawers 60 and 70. As shown in FIG. 5, when front panel 17 and/or door 36 are removed or opened, light drawers may be moveable (or even completely removable) into and out of fluid treatment module 28. Light drawers 60 and 70 may include slides 99 (FIG. 6) attached to the bottom surface of drawers 60 and 70. Slides 99 rest and move on brackets 96 and slide mounting blocks 98 of framework 38 as shown in FIG. 5. Light drawers 60 and 70 may also include handles 84 for grasping during insertion and removal.

Figure 6:
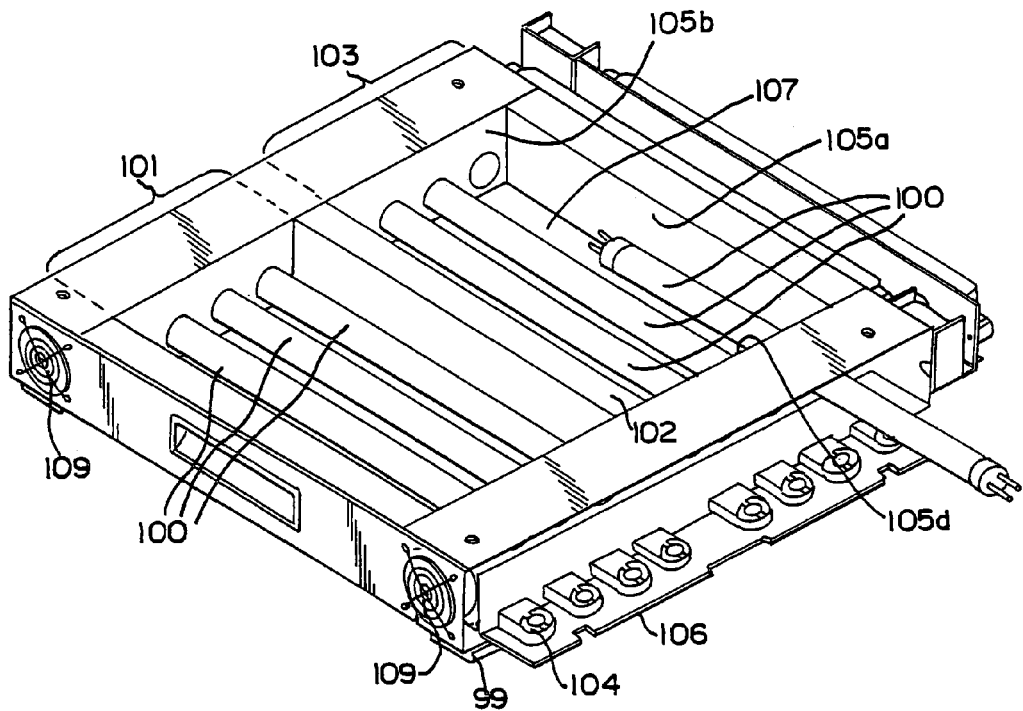
FIG. 6 is a perspective view of a light drawer with socket panel open.

As shown in FIGS. 6, light drawer 60 and/or 70 may be divided into two or more chambers 101 and 103 separated by dividing wall 102. Dividing wall 102 minimizes light from one light chamber of radiating into the other light chamber. This ensures that the light emitted from each lamp or lamp array and contacting the biological fluid is substantially constant. In addition, each of the lamp arrays within light chambers 101 and 103, may be independently monitored and controlled from control module 26. Thus, when one array of lamps is turned off, the other array of lamps may remain on. As described in more detail below, this may be particularly useful where two or more containers of biological fluid requiring different levels of treatment are being treated.

Each of light chambers 101 and 103 of light drawer 60 or 70 is generally defined by four side walls 105 *a-d* and a bottom wall 107. Walls 105 *a-d* and 107 may be made of or coated with a reflective material to maximize the amount of light delivered to the biological fluid. In one specific embodiment, where the light source provides light in the ultraviolet A (UVA) range, walls 105 *a-d* and 107 may be made of a highly reflective aluminum to provide substantial reflection of UVA light. Such a material is sold under the name 1500 G-2 and is available from ALANOD of Ennepetal, Germany.

The light sources suitable for use in the present invention may include any light source that is capable of providing light of a particular wavelength and intensity for treating a particular biological fluid. For example, light sources capable of providing white light, red light, infrared, ultraviolet A and/or B light may be used. Light drawers 60 and 70 may include a single lamp or an array of multiple lamps 100. In one embodiment, light source may include standard fluorescent lamps or bulbs capable of providing light of a wavelength in the UVA (ultraviolet A) range. Such lamps may be obtained from Sagyo Denkai of Japan under the product code BL352. Light drawers 60 and 70 further include fans 109 for cooling lamps 100 and, more specifically, ends of lamps 100 at or near the lamp filaments.

As shown in FIG. 6, the ends of lamps 100 are inserted into sockets 104 housed on socket panel 106. Socket panel may also serve as a printed circuit board. Socket panel 106 may be hinged and openable to allow for easy access to lamps 100, easy insertion and removal of lamps 100, and in general, easier serviceability of light drawers 60 and 70.

As shown in FIG. 5, a portion of fluid treatment chamber 40 and, for that matter, fluid carrying drawer 50, are separated from light drawers 60 and 70 by glass plates 110. As shown in FIG. 5, upper glass plate 110 rests on framework 38 and is, generally, held in place by clamps 112 and 114. A lower glass plate 110 separating a portion of fluid carrying drawer 50 from lower light drawer 70 may also be included. Glass plates 110 are substantially translucent to light of the wavelengths used for the treatment of biological fluid. Preferably, glass plates 110 may also filter unwanted light. Alternatively, a separate filter may be provided for placement between the light source and the fluid treatment chamber 40. In one specific embodiment, where treatment of a biological fluid with UVA light is desired, glass plate 110 may be substantially translucent to ultraviolet light within the range to 320-400 nm, but not translucent to light of a wavelength of less than about 320 nm. Such glass plates are commercially available from Schott Glass of Yonkers, N.Y. under the product designation B-270.

As set forth above, fluid treatment module 28 further includes marker assembly 74. Marker assembly 74 may include one or more markers 76*a*-76*d* for marking containers within fluid treatment chamber. One or more markers 76 may be provided to mark containers at different stages of the treatment. Markers 76*a-d* may be punches for punching holes into a portion of the container such as the container flap as described in U.S. Pat. No. 5,557,098, which is incorporated by reference. Alternatively, and more preferably, markers may be stampers for stamping designated portions of a container with ink. Such markers are commercially available from Trodat of Wels, Austria under the product name Printy 4911.

As shown in FIG. 11, marker assembly 74 may include a plurality of markers 76 *a-d* for marking a plurality of containers during different stages of the light treatment. Markers 76 *a-d* may be attached to a bracket 78 which includes a slide 114. Slide 114 is suspended from and movable within track 116 which is attached to the interior framework 38 of light box 10. Thus the entire assembly 74 can be withdrawn from fluid treatment module 28 for reinking, replacement of markers 76 or for general servicing as shown in FIG. 5.

Figure 12:
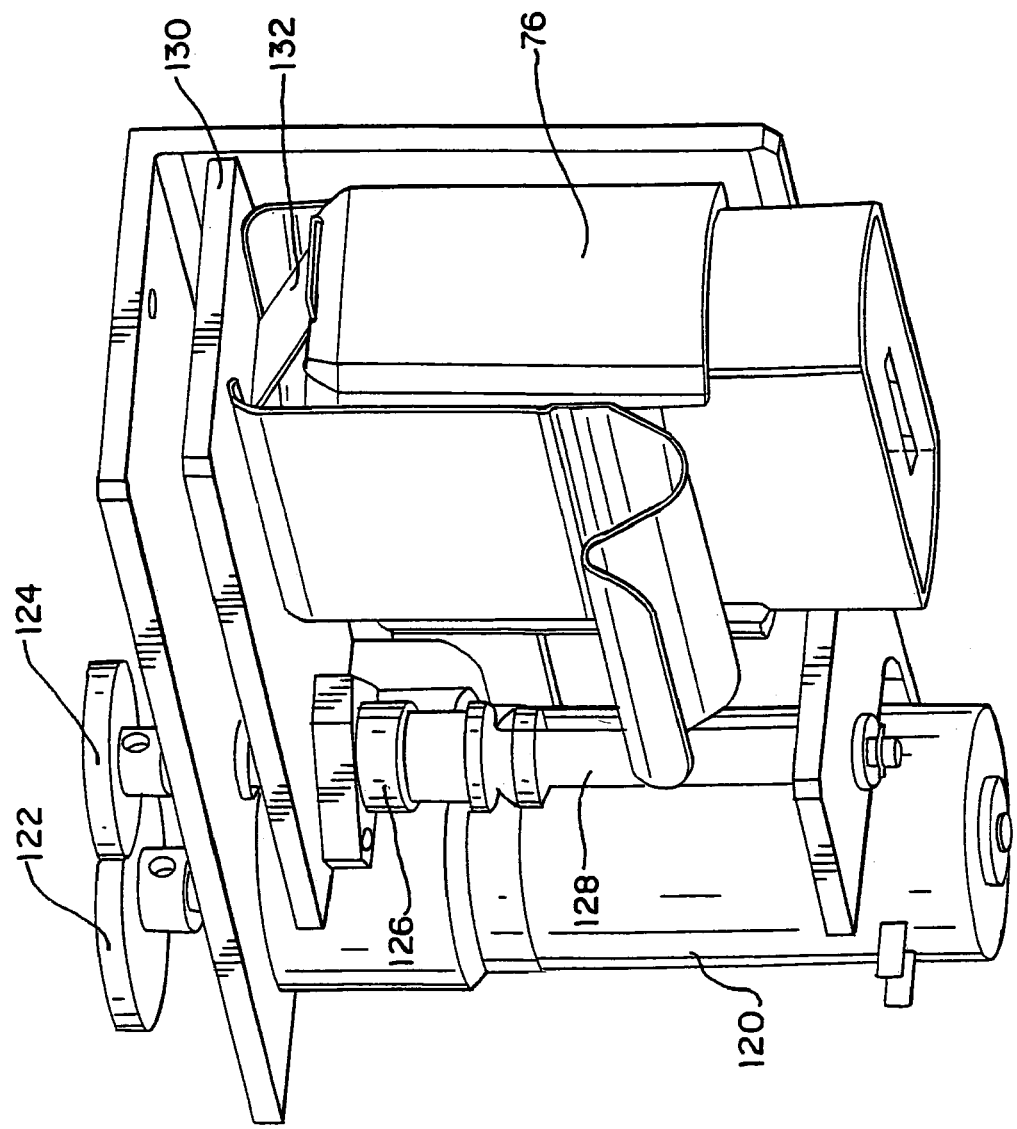
FIG. 12 is an enlarged perspective view of an individual marking unit of the container marker assembly.

As shown in FIG. 12, each individual marker unit includes a marker drive motor 120 that moves markers 76 up and down through gear 122, gear 124, lead screw 128, lead nut 126, bracket 130 and spring 132. Movement of gears 122 and 124 actuates movement of lead screw 128 and causes downward and/or upward movement of lead nut 126, bracket 130 and consequently marker 76.

Fluid treatment module 28 includes blower 134 which provides air flow into fluid treatment chamber 40 and fluid containers and thus, provides for temperature control of fluid treatment chamber 40 (FIG. 5). Blower 134 receives ambient air through an opening in bottom wall 16 located below blower 134. In addition to providing air to fluid treatment chamber 50, air from blower 134 may also pass through opening 136 of fluid treatment module 28 and a perforation or opening 136*a* in control module 26, as seen, for example in FIGS. 2 and 4.

Returning to the fluid treatment module 28 and more specifically fluid carrying drawer 50, as shown in FIGS. 5 and 13, fluid carrying drawer 50 may include a tray 90 for holding one or more containers of biological fluid. Tray 90, shown in FIG. 7, may be placed within the cavity 88 of the fluid carrying drawer 50 (FIG. 8). In one embodiment, tray 90 may be made of a molded plastic material. Where the biological fluid is treated from two sides, the molded plastic material should be sufficiently translucent to the light provided by the lamps 100. Suitable materials for tray 90 include acrylic polymers such as polymethyl methacrylate (PMMA) or members of the polyolefin family such as methylpentene copolymer. Such materials are available from many sources including CYRO Industries of Rockaway, N.J. under the product name ACRYLITE® OP4 or from Mitsui Plastics of White Plains, N.Y. under the name TPX.

Where one or more containers are to be treated, tray 90 may be divided into a first portion 180 and a second portion 182 separated by dividing wall 184. As shown in FIG. 7, tray 90 may include retaining tabs 186 for placing a slit or other aperture of a biological fluid container 206 over tab 186 to limit movement of the container within tray 90 and ensure that the container is substantially within the field of light provided by the light source. The volume of tray 90 should be sufficient to hold at least the entire volume of biological fluid contained within the containers so as to minimize the risk that, in the event of container leakage, liquid will overflow and contact the electrical and mechanical components of light box 10, even during agitation.

Where the biological container is part of an integrated fluid processing set, tray 90 may be compartmentalized to provide separate compartments for the container undergoing treatment on the one hand, and the remainder or a portion of the remainder of the disposable processing set, on the other hand. As shown for example, in FIG. 7, first portion 180 and second portion 182 each include a first compartment 188 and second compartment 190 separated by discontinuous wall 192. First compartment 188 may hold a container of biological fluid 206 and the second compartment may hold the remaining components of the fluid processing set. A slot in the wall 192 accommodates the tubing that connects container 206 with the remainder of the disposable processing set. Tray 90 or second compartment 190 of tray may further include container retaining tabs or pegs 193 to assist in holding the containers in the second compartment in place and limiting movement of such containers within tray 90.

When the tray 90 with disposable processing set is introduced into fluid treatment chamber 50, container 206 within a first compartment 188 is positioned substantially within the field of light provided by the light source. The remainder of the disposable processing set and/or containers within a second compartment 190 are aligned substantially with marker assembly 74 as shown in FIGS. 4 and 5. Thus, the status of the treatment may be indicated on the other containers of the processing set within the second compartment 190 by markers 76 *a-d*.

Light box 10 may include sensors for detecting different conditions during the pretreatment and treatment process. The sensors relay signals to the microprocessor of the light box 10 which is housed within control module 26. As shown for example in FIG. 14, sensors (e.g., 404, 430) send signals through the sensor input/output board 33 which translates the signal into a format that is understandable by microprocessor 160. The computer alerts the operator, either by an audible alarm or a message on the display screen 37. The operator may, in response to the alarm or message, take action through keypad 39. Alternatively, in response to certain alarm conditions, the control system may be preprogrammed to automatically take action, such as terminate treatment, if necessary.

For example, light box 10 may include internal light intensity sensors 404 for measuring the intensity of light provided by the lamps 100 to fluid treatment chamber 50. In the event that the light intensity provided by lamps 100 is insufficient for the desired treatment, sensor 404 sends a signal through input/output board 170 (FIG. 14) to microprocessor 160 as described above.

In one embodiment, light intensity sensors 404 may be located within the light chambers 101 and 103 of light drawers 60 and 70 (FIG. 6). In one embodiment, light drawer 60 and/or 70 include a light intensity sensor subassembly 402 on the underside of drawer 60 and/or 70. As shown in FIG. 6*a*, subassembly 402 includes two or more sensors 404 attached thereon and placed within sensor windows 406 located in the bottom wall 107 of drawers 60 and/or 70. Sensor windows 406 allow light from lamps 100 to pass through and contact sensors 404. Sensors 404 may include or be used with one or more filters to filter out unwanted light. More specifically, where light box 10 is used to activate a photochemical agent, it may be desirable that the filters used in association with sensors 404 have a maximum sensitivity in the wavelength range that substantially matches the wavelength range within which the particular photochemical agent is most effectively activated (i.e., the "action curve"). This allows sensor 404 to detect the effectiveness of photochemical activation. Such sensors are available from Texas Advanced Optoelectronics Solutions under the product code TSL230B. Filters are available from a variety of sources such as Schott Technical Glass of Duryea, Pa.

A fluid carrying drawer sensor 144 may be included for monitoring the position of fluid carrying drawer within fluid treatment chamber 40. Fluid carrying drawer positioning sensor 144 ensures that the drawer 50 is in a fully closed position and therefore, that containers of biological fluid are substantially within the field of light provided by lamps 100. If the drawer is not in a fully closed position, sensor 144 sends a signal to the microprocessor, alerting the operator and preventing treatment from proceeding.

Light box 10 may further include temperature sensors 145 for either directly or indirectly monitoring and measuring the temperature within fluid treatment chamber 40. Temperature sensor may be disposed within the fluid treatment chamber 40 or, as shown in FIGS. 4 and 5, may be disposed on the exterior of light box 10 to measure the ambient temperature of the outside environment. For example, ambient temperature sensor 145 may be located anywhere on the surface of light box 10. In one embodiment, as shown in FIGS. 1 and 2, ambient temperature sensor 145 is placed at or near control module 26. Ambient temperature sensor 145 provides an indication of the air temperature being delivered to fluid treatment chamber by blower 134. In the event that the temperature falls outside of a predetermined temperature range, the ambient temperature sensor sends a signal to the microprocessor as generally described above, which alerts the operator that the temperature is approaching or has exceeded its limit. Accordingly, the operator and/or instrument may take further action.

Figure 11A:
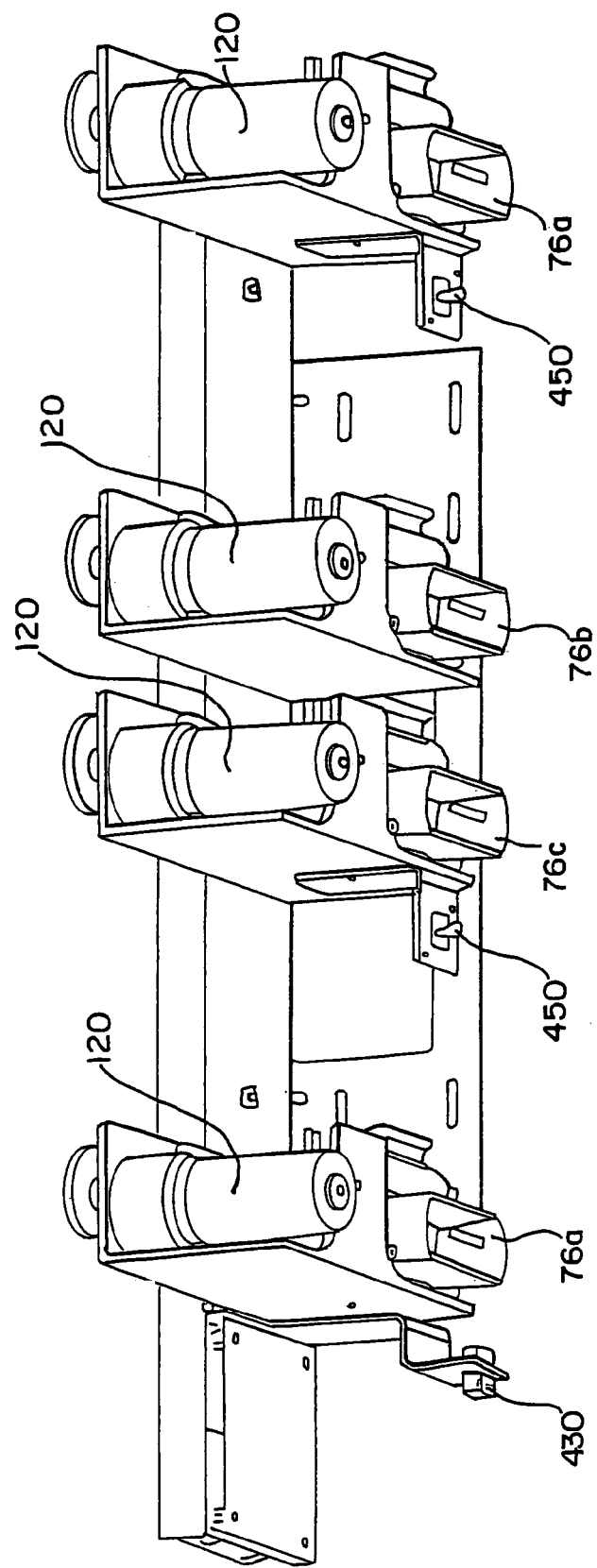
FIG. 11A is another perspective view, from the underside, of the container marker assembly.

Additional sensors may be provided, including a sensor for monitoring the agitation provided by the agitation assembly. Sensor 430 may be attached to marker subassembly 74, as shown in FIG. 11A, and measures movement of the agitation assembly described above. In one embodiment, sensor 430 may include an infrared source such as, but not limited to a light emitting diode (LED) or laser that contacts a selected reflective portion of the agitation assembly. If sensor 430 does not detect reflection or does not detect reflection at the predetermined frequency, it signals the microprocessor accordingly.

Light box 10 may also include a sensor 440 to detect whether the front door of the light box is closed during treatment. Door sensor may be a magnetic switch which detects contact between door 36 and magnetic plate 441 shown in FIG. 3. Also, plunger switch 36*a* (FIG. 4) is pressed when door 36 is closed. If door 36 is open, plunger switch 36*a* serves as an electrical cut off. If, the door is open, the system will not permit the treatment to proceed.

Light box 10 may also include sensors 450 for determining whether containers are in position for marking by markers 76. As shown in FIG. 11A, sensors 450 may be attached to markers 76 and may include optical receivers aligned with light emitting diodes (LED) (not shown) typically located below fluid carrying tray 90. The labels of containers placed within the second compartment 190 of tray 90 prevent optical receiver 450 from receiving the LED signal, indicating the presence of a container. Conversely, if sensor 450 receives the signal, this indicates that no container is present and the marker will not be activated. In addition, each marker 76*a-d* may include a microswitch (shown as 470 in FIG. 14) to detect whether movement of the marker has occurred and to prevent mechanical failure or damage the parts that make up the marker.

In addition, a portable and attachable light intensity sensing, verification and calibration device or radiometer 460 may be provided to verify light intensity provided by light box 10 and for calibration of light box 10. Radiometer 460 may be adapted for placement within fluid treatment chamber 40 for measuring the energy dose delivered to the biological fluid. More specifically, radiometer 460 may be adapted for placement within the fluid container carrying tray 90. In one embodiment, radiometer 460 may be adapted for placement within a compartment of tray 90 such as first compartment 188 of tray 90.

Figure 14A:
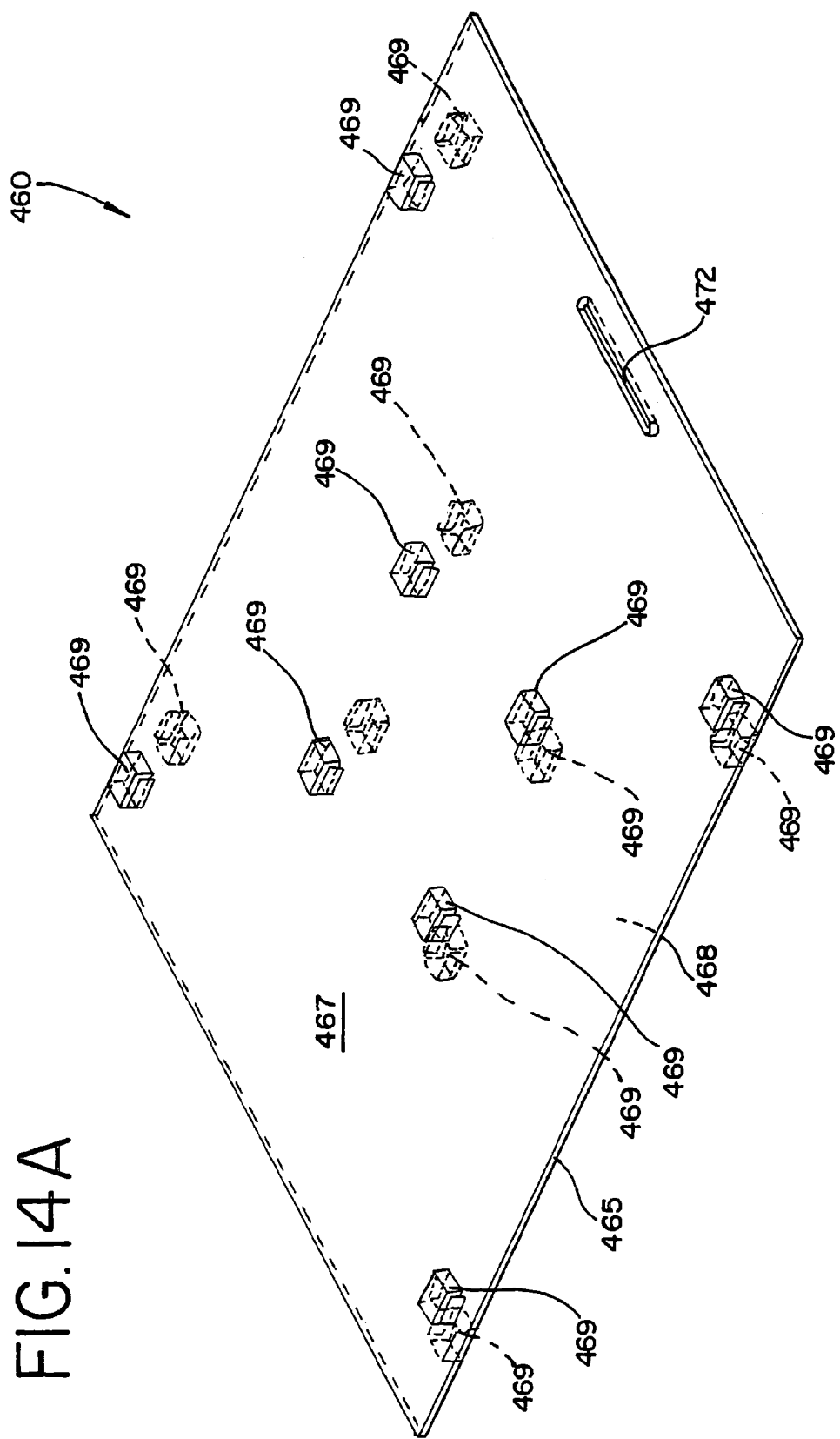
FIG. 14A is a perspective view of a light sensing device which may be used with the apparatus of FIG. 1.

As shown in FIG. 14A, radiometer 460 may include a support 465 having a top surface 467 and a bottom surface 468. Support 465 is typically a printed circuit board. One or more sensors 469 are electrically and physically connected to support 465.

It is known that a light source may not always uniformly emit light. For example, depending on the age of the lamp, the intensity of light emitted from one part of the lamp may not be the same as the intensity emitted from another part of the lamp. Accordingly, in a preferred embodiment, as shown in FIG. 14A, radiometer 460 may include a plurality of sensors spaced across the top and/or bottom surface(s) to receive light from different points on one or more lamps. Also, sensors 469 may be placed on one side of support 465, but preferably are placed on both the top surface 467 and the bottom surface 468. Top and bottom placement of sensors 469 is particularly preferred where radiometer 460 is used to measure light provided by two facing light sources, such as in one of the embodiments of light box 10.

An electrical cord (not shown) is attached to radiometer 460 for electrical connection to light box 10 and, for example, port 461 (FIG. 5). This allows radiometer 460 to transmit data to the computer-based control system of light box 10, which system provides information to the operator and/or automatically takes action based on the transmitted data. Radiometer 460 may also include a slit 472 for placement over tab 186 in tray 90 of light box 10.

Sensors 469 may typically be photodiodes capable of detecting light of selected wavelengths. Sensors 469 may also include or be used with filters to filter out unwanted light as substantially described above.

When used in connection with light box 10, it is preferred that the dimensions of radiometer 460 be substantially equivalent to the dimensions of the fluid-filled containers used with light box 10. Accordingly, it is preferred that the light sensing area of radiometer 460 have a height, a width and a thickness substantially equal to such filled containers. A radiometer with dimensions substantially equal to the fluid-filled container provides a reliable approximation of the energy being delivered to the fluid and of the effectiveness of the treatment.

As set forth above, radiometer 460 may be used for light intensity verification by, for example, the operator and for calibration of light box 10 generally and more specifically, of internal sensors 404. In accordance with the method of using radiometer 460 for light intensity verification, the operator may place radiometer 460 in first compartment 188 of tray 90. Cord may be pressed into strain relief tabs 474 within light box 10 (FIG. 8). The fluid carrying drawer 50 is inserted into fluid treatment chamber 40 and door 36 is closed. Lamps 100 are turned on and the light delivered is measured by sensors 469. Specifically, the light measured by sensors 469 is processed by the system's microprocessor to provide a reading of the energy being provided to the fluid treatment chamber 40. The operator can monitor the output of lamps 100 and determine any diminishment in the lamp output by comparing the reading to a pre-set acceptable energy dose range. In addition, the readings provided by sensors 469 are also compared to the readings provided by sensors 404 to detect any diminished sensing capability of sensors 404.

Thus, for example if the energy dose measured by radiometer 460 is substantially equal to the energy dose detected by sensors 404, but is outside the pre-set dose range, this may be an indication that the output of lamps 100 has diminished and that lamps 100 may have to be replaced. Alternatively, if the energy dose as measured by radiometer 460 is substantially equal to the expected pre-set dose of the instrument, but both are different from the energy dose as measured by sensors 404, this may be an indication that sensing capability of sensors 404 has diminished. Finally, if the dose as measured by sensors 404 is substantially equal to the expected pre-set dose, but different than the energy dose as measured by radiometer 460, this may indicate that the sensing capability of radiometer 460 has diminished. Radiometer may also be used to calibrate light box 10. Radiometer 460 itself may be calibrated against a standard (e.g. a standard from the National Institute for Standards and Technology or NIST).

Of course, it will be appreciated that radiometer 460 may have utility in other applications and is not limited to use in the apparatus or methods of the present invention. Indeed, radiometer 460 may be used whenever light is to be measured over an extended surface area.

The components of the fluid treatment module 28 including the agitator assembly, the light sources, the blower, the marker subassembly are powered by power supplies as shown in FIG. 14. (In FIG. 14, the letter "n" represents the number of electrical or mechanical components such as sensors, lamps, ballasts etc.). For example, power supplies (ballasts) 166 power lamps 100 and are controlled and supplied by relay board and isolation transformer 29. Shaker motor 92 is powered through relay board and isolation transformer 29. Additional power supply 168 supplies power for the blower 134, light drawer fans 109, and drive motors 120 for markers 76a-d and door lock 480. Preferably, the power supply for powering these components may be approximately 24 volts DC. Power supply 167 may supply +5, +12, -12 volts DC to, for example, computer board 160.

Finally, light box 10 includes a programmable computer software-based control system to control the operation of light box. The control system is generally and diagrammatically depicted in FIGS. 19-23 and is described in greater detail in connection with the description of the method of processing and treating a biological fluid which follows the description of the disposable processing set provided below.

b. Disposable Processing Set

Disposable processing sets useful with light box 10 are shown in FIGS. 15-18. Typically, the disposable processing set will include two or more plastic containers integrally connected by plastic tubing. At least one of the containers should be suitable for holding the biological fluid during light treatment. The other container should be suitable for storage of the biological fluid after treatment. As described in more detail below, the disposable processing set may be joined with containers of biological fluid, and the fluid may be transferred to containers of the disposable processing set.

Figure 15:
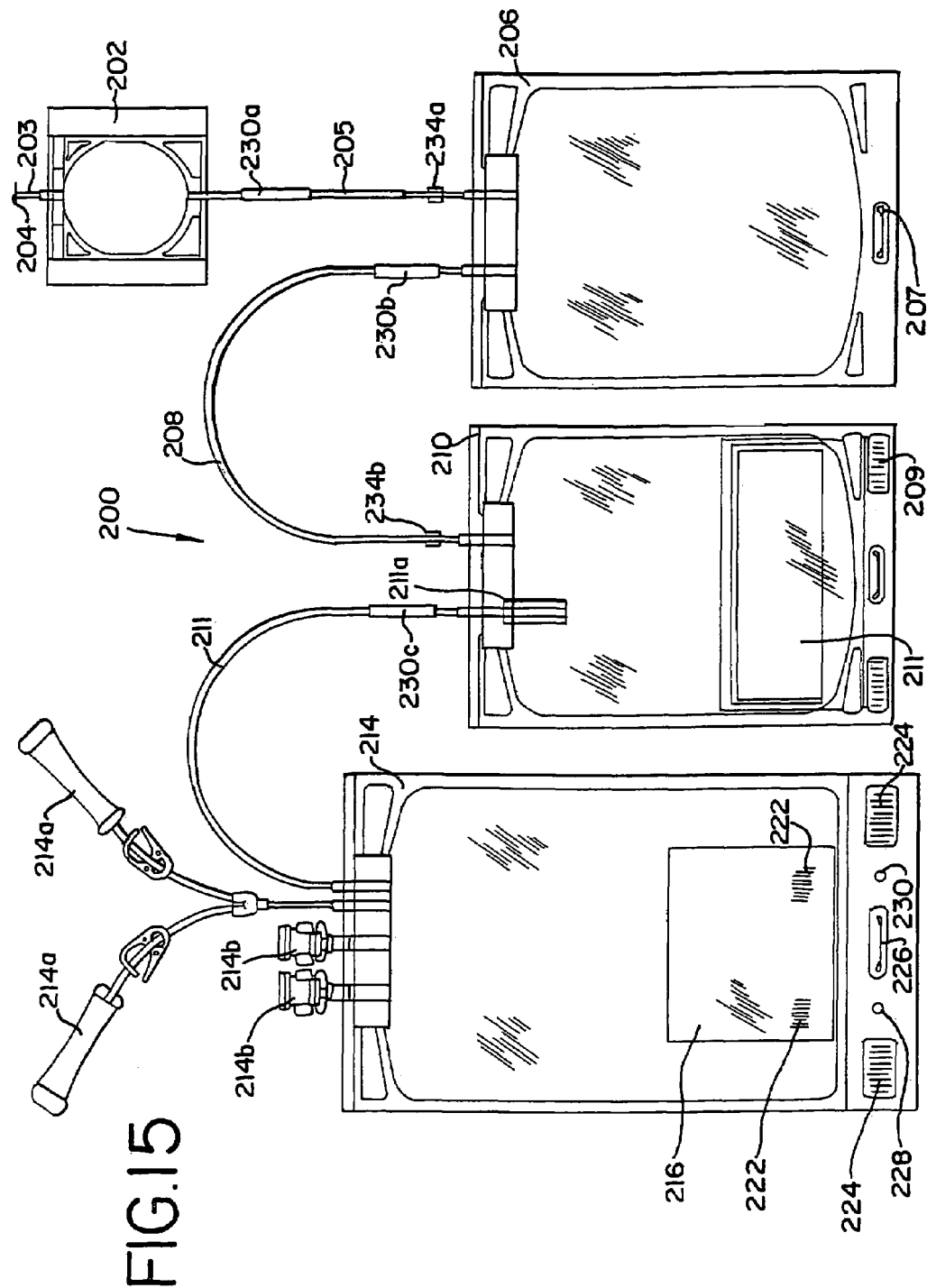
FIG. 15 is a plan view of a disposable fluid processing set embodying the present invention.

One embodiment of a disposable fluid processing set 200 is shown in FIG. 15. Processing set 200 includes a container 202, a container 206, a container 210 and a container 214. The containers may be integrally interconnected with tubing segments as generally shown and described in detail below. The sizes and internal volumes of containers 202, 206, 210 and 214 may vary depending on the biological fluid being processed. In a non-limiting example, container 202 may be capable of holding approximately 15-30 ml of fluid, containers 206 and 210 approximately 1000 ml and container 214 between approximately 1000-1500 ml. Of course, other desirable sizes and volumes may be used and are within the scope of the present invention.

Where the disposable processing set is used in or as part of a pathogen inactivation treatment, container 202 may include, for example, a photochemical agent which is mixed with the biological fluid. Examples of such photochemical agents include psoralen compounds described in U.S. Pat. No. 5,709,991 and compounds from the family of phenothiazine dyes such as, but not limited to, methylene blue. Container 202 may be made of any material suitable for holding such photochemical agents. One such material may be a blend of ethylene polypropylene, polyamide and a block copolymer of ethylene and butylene with terminal blocks of polystyrene. Containers made of such material are available from Baxter Healthcare Corporation under the name PL2411. Container 202 includes a tubing segment 203 extending therefrom and having a sealed end 204. A second tubing 205 extending from container 202 is integrally connected to container 206. In another embodiment, the photochemical agent may be contained or predisposed within container 206, thereby eliminating the need for a separate container 202 for holding the photochemical agent. In still another embodiment, the photochemical agent may be combined with the biological fluid prior to joinder to the disposable processing set. For example, the photochemical agent may be included in a container 201 used to hold the biological fluid collected from a donor (FIG. 17).

Container 206 is preferably a container suitable for holding the biological fluid during light treatment. Accordingly, it is desirable that container 206 be made of a clear, durable, thermoplastic material that is translucent to light of the selected wavelength and sterilizable by known forms of sterilization including steam sterilization, gamma and electron beam radiation. For example, where the blood product to be treated includes blood platelets or blood plasma and the treatment is to be with light in the UVA range, container is made of a material that is substantially translucent to UVA light and remains stable after sterilization. Such materials may include polyvinyl chloride, but more preferably, may be blends of thermoplastic polymers and copolymers, including general purpose polymers, elastomers and the like. One such material includes the block copolymer described above which includes a central block of ethylene and butylene and terminal blocks of polystyrene. Block copolymers of the type described above are available from the Shell Chemical Company under the name KRATON. The block copolymer may be blended with other polymers such as ultra low density polyethylene (ULDPE) and ethylene vinyl acetate (EVA). Containers made of the blended material are available from Baxter Healthcare Corporation of Deerfield, Ill. under the name PL-2410. Other thermoplastic materials may also be suitable for container 206, including materials including KRATON, EVA, and polypropylene. A container made from such material is also available from Baxter Healthcare Corporation under the name PL-732. Still other suitable materials for container 206 include fluoropolymers such as polytetrafluoroethylene (PTFE), PFA or copolymers including such fluoropolymers.

Container 206 further includes a slit 207 which, as described above, may be placed over retaining tab 186 in tray 90. Container 206 includes a tubing segment 208 which may be integrally connected to a container 210.

In the pathogen inactivation of biological fluid, container 210 may, for example, include an adsorbent material 211 for removing excess photochemical agent or the byproducts of the photoactivation process. The adsorbent material may be contained in a semi-permeable pouch, preferably affixed to the container walls or portions thereof within the interior chamber of container 210. The interior chamber of container 210 has a volume sufficient to hold the biological fluid from container 206. Such a container and the adsorbent material are disclosed in more detail in copending patent application entitled "Plastic Containers Having Inner Pouches and Methods for Making Such Containers" which is being filed simultaneously herewith in the names of Mahmood Mohiuddin, George D. Cimino and Derek J. Hei, and is incorporated by reference in its entirety. Materials such as those used in the PL-2410 and PL-732 containers described above are suitable for use in container 210.

Container 210 may also include a time-sensitive tape 209. Tape 209 changes color with time, thus informing the operator if the biological fluid has contacted the adsorbent material for a sufficient period of time. Container 210 may be integrally connected by tubing segment 211 to another container 214 which may be suitable for storage of the biological fluid. As shown in FIG. 15, the portion of tubing segment 211 that communicates with the interior of container 210 may include a filter 211a to capture loose particles of adsorbent, if any.

Container 214 may include and/or be capable of receiving a label 216 which may carry bar codes 222 or other indicia which provide information about the biological fluid. For example, bar codes 222 may identify the donor, the product, the lot number of the biological fluid, expiration date and the like. Container 214 may include additional bar codes or indicia 224 which are used to provide information regarding the status or progress of the fluid treatment (described in more detail below). Container 214 may also include a slit 226 and/or apertures 228, 230 for placement over corresponding pegs (193) on tray 90. Materials such as those described above are suitable for use in container 214. Container 214 may also include sampling pouches 214a and access ports 214b to allow for fluid access during later transfusion, as will be recoginzed by those of ordinary skill.

In an alternative embodiment, disposable processing set may include a single container for housing the adsorbent material of container 210 and for storing the biological fluid, thereby combining the functions of container 210 and 214 described above.

The disposable processing set 200 described herein may further include frangible members 230 (a-c) disposed within tubing segments as shown in FIG. 15. Frangible members 230 are broken at the appropriate time to establish fluid communication between the containers of the processing set 200. Such frangible connectors are described in detail in U.S. Pat. No. 4,294,297 which is incorporated by reference herein. Tubing segments of disposable processing set 200 may further include indicators 234a and 234b on the tubing to indicate proper positioning of the disposable processing set within the tray 90 (as will be described more detail below) and/or to serve as indicators of where tubing is to be severed and sealed. In one embodiment, indicators 234 may be plastic rings disposed around tubing segments. Of course, other tubing indicating means may be used.

Figure 16:
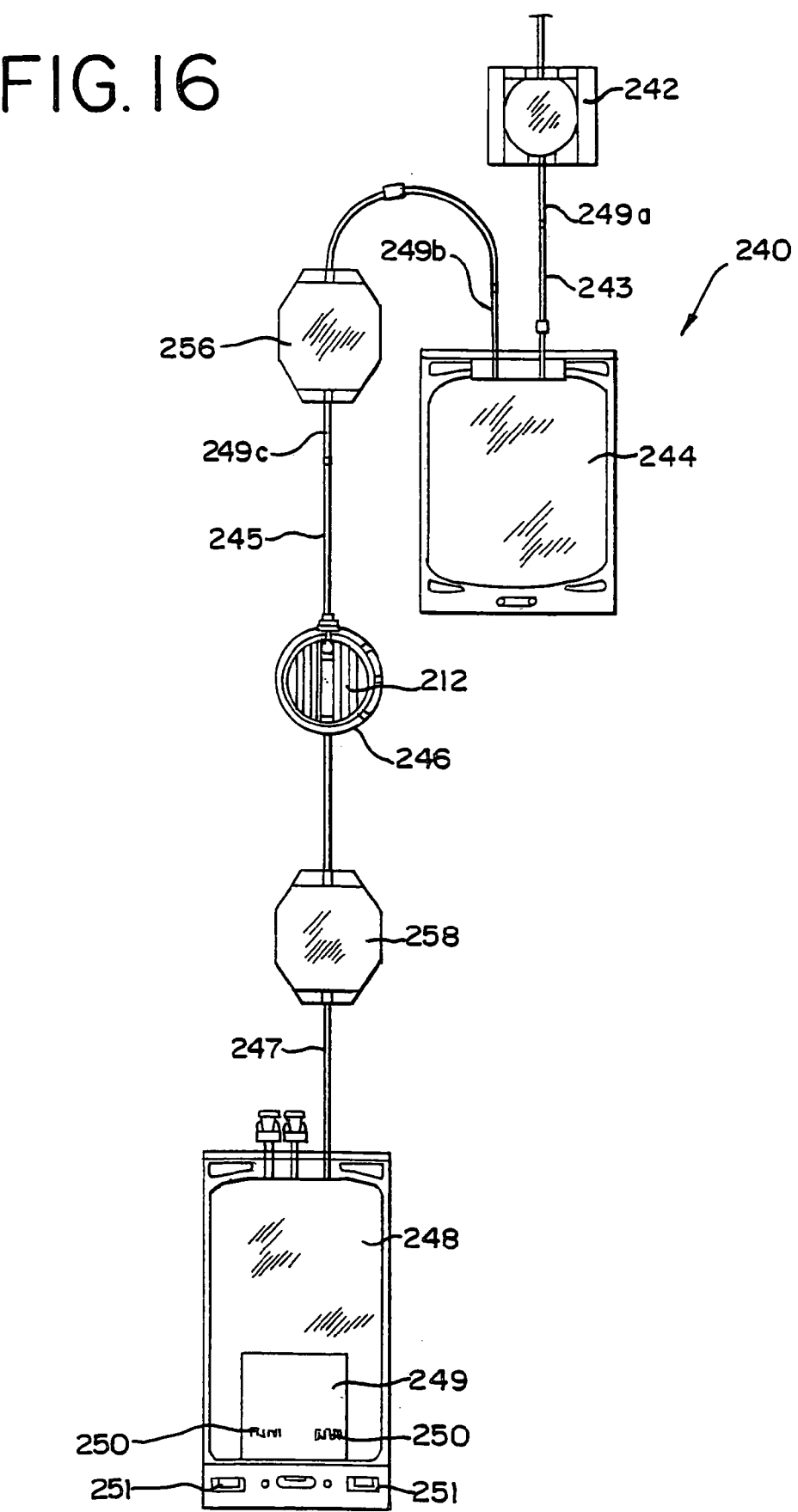
FIG. 16 is a plan view of another disposable fluid processing set embodying the present invention.

Another embodiment of a fluid processing set is shown in FIG. 16. In FIG. 16, disposable processing set 240 also includes a container 242 which carries a photochemical agent, a container 244 which holds the biological fluid during light treatment, a container 246 which includes an adsorbent material for removing excess photochemical agent and/or the byproducts of the photoactivation process, and a container 248 suitable for storage of the biological fluid. Container 248 is adapted to receive label 249 with bar codes or other indicia and may include additional indicia 251 including, for example, additional bar codes as substantially described above.

In contrast to the container 210 of the earlier described embodiment, container 246 is a flow through device which includes adsorbent material 212 but does not include a chamber for holding the biological fluid for any significant period of time. Such flow through devices are described in International Publication No. WO 96/40857 which is incorporated by reference herein. Disposable processing set 240 may further include an air reservoir 256 and air sink 258. Air reservoir 256 provides air to help expel biological fluid from container 244 and air sink 258 receives excess air expelled from storage container 248 after processing. Air reservoir 256 and air sink 258 may be made of any suitable biocompatible material, including the materials described above. Likewise, the containers of disposable processing set 240 may also be made from the materials generally described above. Preferably, container 256 is substantially impermeable to air.

As in the embodiment of FIG. 15, the containers of disposable processing set 240 shown in FIG. 16 may be integrally interconnected by tubing segments 243, 245 and 247. Tubing segments may further include frangible members 249 (a-c) for opening fluid communication between the containers.

Disposable processing set 200 (or 240) is typically provided to the user in a sealed package in a manner that is easy for the user to unpack and use. For example, upon opening the package, it is preferred that the container to be used first in the fluid processing be located near the top of the package. For example, in the processing set 200 shown in FIG. 15, container 202 would be located near the top of the package, followed by container 206, followed by the remainder of the disposable processing set that includes containers 210 and 214. In addition, if disposable processing set includes container 202, (or 242 in the embodiment of FIG. 16) at least such container should include a separate and additional light impermeable overwrap to protect the contents (i.e. the photochemical agent) from exposure to light which could result in premature activation of the photochemical agent. In one embodiment, the light impermeable overwrap may be permanently sealed to the outer walls of container 202.

In a preferred embodiment, containers 210 and 214 may be contained within or held together by a holder. Holder may be any device such as a clamp that holds together containers 210 and 214. The holder may be integral with the disposable processing set or may be provided separately.

More preferably, holder 260, shown in FIGS. 17-18, may be a receptacle or other shell-like holding device. In one embodiment, holder 260 may include a bottom wall 262 which separates the containers 210 and 214 from container 206. In a preferred embodiment, holder 260 may have sidewalls 262 and 264, a back wall 268 and includes a substantially open front portion as shown in FIGS. 17-18. In addition, bottom wall 262 may include a slot 263 to accommodate tubing that connects containers of disposable processing set 200. Holder 260 may also include additional side openings 265 (shown, for example, in FIG. 17) for holding tubing segments of container 202 prior to unpackaging of the disposable processing set. Holder 260 may be made of any suitable material such as but not limited to plastic or cardboard. Preferably, holder 260 is made of a moldable plastic material that may be sterilizable and impact resistant.

Alternative embodiments of holder 260 are shown in FIGS. 18A-18D. As shown in FIGS. 18A-18C, holder may include two frame or partial frame portions 600 and 602. Frame portions 600 and 602 may be joined and include hinge 604 as shown in FIG. 18B and 18C. Alternatively, frame members 600 and 602 may be completely separable as shown in FIG. 18D. Frame portions 600 and 602 include means for securing together the frame portions such as mating slots 605 and pins or lugs 606 as shown. Holder 260 shown in FIGS. 18A-18D includes a central opening 608 to allow the label of a container placed within holder 260 to be exposed to the outside environment to allow scanning by, for example, a bar code reader and/or marking by markers 76 as described below.

In one embodiment, container 210 is placed in the front portion of holder 260, such that a label to be applied to the container 210 and other indicia on the container itself are exposed to the outside environment through the open portion of holder 260 as shown in FIG. 17. For purposes of illustration, in FIGS. 17-18, label is shown as applied to container 214. In one embodiment container 214 may not include label at the time of use and a label may be transferred to container 214 from a container of biological fluid. Alternatively, container 214 may include a label and an additional label may be transferred from a container of biological fluid. In any event, container 214 may be folded in half (or tri-folded) with container 210 (also folded) placed behind container 214. In addition, folded container 214 may be lightly spot welded at its ends to keep the container folded and improve handleability of the container. The weld should be sufficiently strong to keep container 214 in a folded position, but not so strong that undue force applied by the user would be required to disconnect the welded ends. Spot welded ends of container 210 should release when tugged gently by the user.

c. Methods of Processing and Treating Fluid

The method of processing fluid using disposable processing set 200 (or 240) and treating a biological fluid with light in, for example, light box 10 will now be described. Although the following description will be provided in the context of processing the biological fluid for subsequent inactivation of pathogens in the biological fluid, it should be understood that many of the steps described below may also be carried out in other fluid processing and treating methods that do not involve pathogen inactivation. The following description will be provided using the disposable processing set of FIG. 15 as an example, although it will be understood that the description may also apply to other processing sets, such as the set of FIG. 16.

In accordance with the method of processing a biological fluid such as blood using the processing set 200, a container of collected blood or biological fluid is provided. Although the method of collection is beyond the scope of the present application, representative methods of collecting blood products include the automated and manual centrifugal processing, separation and collection of blood products, membrane separation of blood products and the like. One example of a centrifugal blood processing system is the AMICUS® Separator sold by Baxter Healthcare Corporation.

Regardless of the collection method, containers of the collected blood product will typically bear a label that includes information identifying the donor, the blood product and lot numbers. Most typically, such information is presented in the form of one or more bar codes on the label which can be scanned and read by bar code reader, such as bar code reader 41 of light box 10. Such labels may be removable and transferable to container 214 of the disposable processing set 200.

Typically, the collection container will include a tubing segment extending therefrom. Accordingly, tubing from the collection container 201 and tubing segment 203 from the disposable processing set 200 are brought together and joined in a sterile manner, as shown generally in FIG. 17. A device that is useful for the the sterile joinder of tubing portions is available from Terumo Corporation of Japan and sold under the name Terumo SCD. This device heat seals two opposing tubing portions in a sterile manner. The heat from the heat sealing kills any bacteria from the outside environment that may enter or reside in the tubing segments, thereby preserving the sterility of the entire processing set. Of course, any method and apparatus for joining two tubing segments while maintaining sterility may be used.

Once tubing segments have been joined, frangible member 230a is broken to provide an open flow path from the collection container 201 to the container 206 (FIG. 15). Photochemical agent from container 202 is also allowed to flow into container 206. After fluid transfer to container 206, tubing segment may be severed and sealed and the portion of the disposable processing set that included container 202 and the collection container(s) 201 are discarded. Indicator 234a provides a reference point as to where the tubing is to be severed. It is preferable that the indicator be placed as close as possible to the container 206 so that most of the biological fluid is retained within container 206 where it is most likely to be mixed and treated.

Before or after placement of the disposable processing set in tray 90, operator may scan the label and other container indicia with bar code reader 41. Bar codes 222 on the main container label 216 or the container itself provide the instrument with information regarding the biological fluid to be treated. Based on the data, the light treating instrument or operator prescribes the light dosage and then calculates the duration of the treatment.

Container 206 of disposable processing set 200 is typically placed in first compartment of tray 90. Slit 207 in container 206 is placed over retaining tab 186 in first compartment 188 and holder 260 with containers placed therein are placed within the second compartment 190 of tray 90. Slits and/or apertures in container 216 are likewise placed over retaining tabs or pegs 193 in second compartment 190. Tubing connecting container 206 with container 210 (and/or 214) may be pressed into the slot in wall 192. It is preferable that the tubing be positioned parrallel to the direction of the side-to-side oscillation provided by the agitator assembly described above. This further ensures that any fluid within tubing segment 208 is also mixed. Indicator 234b not only serves as a reference point for severance of the tubing but also serves as a reference point for container placement by ensuring that substantially the entire container and biological fluid therein is within the field of light. The indicator has a diameter greater than the width of the slot.

Once the containers are in their respective compartments of tray 90, fluid carrying drawer 50 is closed. As set forth above, plunger switch 36a (FIG. 4) is pressed when door 36 is closed. If door 36 is open, plunger switch 36a serves as an electrical cut off. If, the door is open, the system will not permit the treatment to proceed.

Light box 10 includes a programmable computer software-based control system to control the operation of light box 10. The control system is generally and diagrammatically depicted in FIGS. 19-23. As shown in FIGS. 19-23, the system tests, monitors and controls various aspects of the light box 10 and treatment operation such as the start up, container loading, container treatment and container unloading stages of the light box operation. The control system allows the operator to take action or advises the operator of the treatment status through either an alphanumeric or a graphical user interface displayed on screen 37. The various functions may be initiated by the operator through control panel or automatically by the control system itself.

Figure 19:
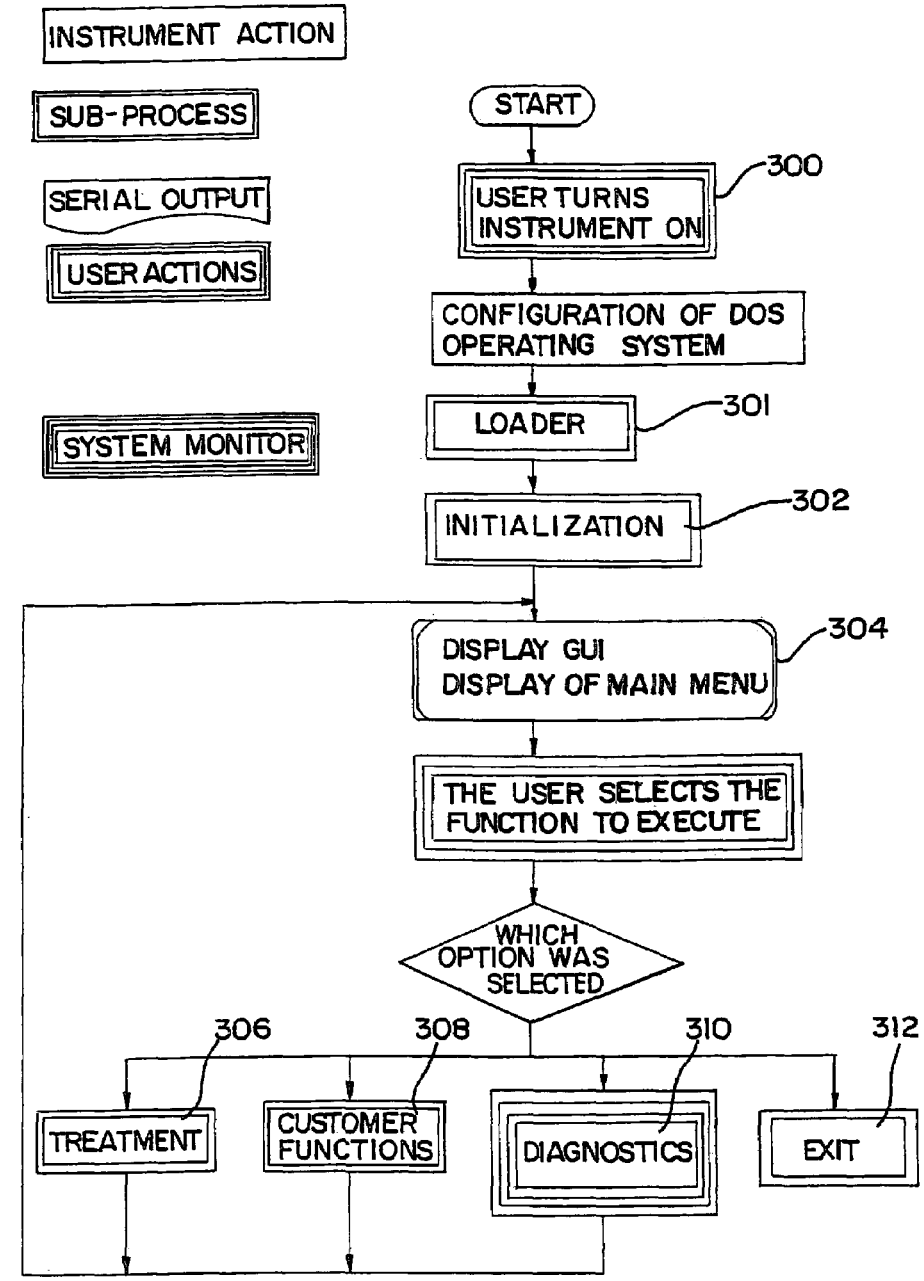
FIG. 19 is a flow chart showing the start-up phase of the control system for the present invention.

For example as shown in FIG. 19, after the operator has turned on the instrument (step 300), the control system will initiate a series of steps including loading the software 301, initializing the software 302, and displaying the graphical user interface screen and menu 304. The operator may then select from the series of available functions including the treatment function 306 or general user function 308. Alternatively, the operator may choose to exit the system 312. Diagnostic checks 310 may also be selected and performed, typically by a service technician.

Figure 20A:
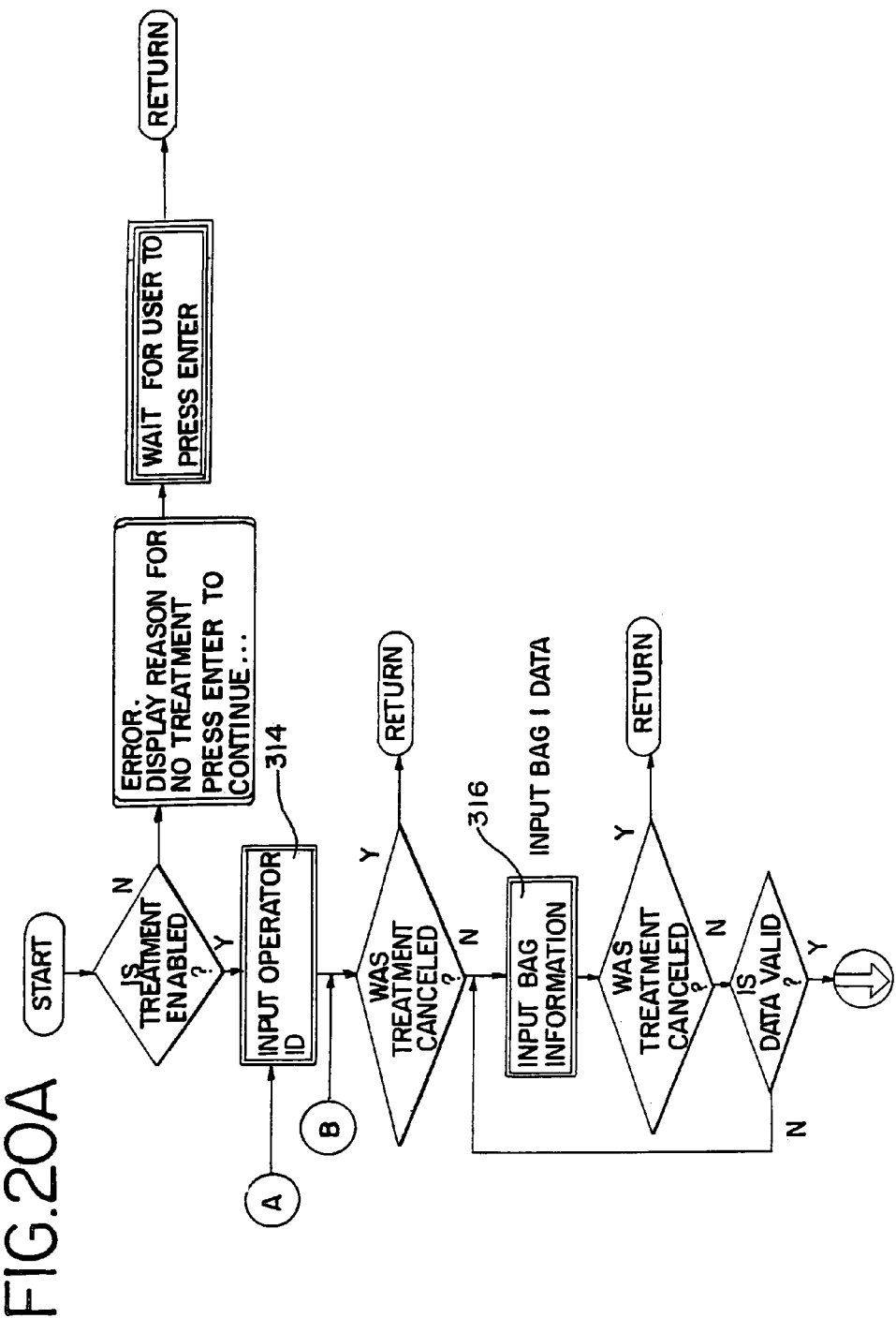
FIG. 20A is a flow chart showing the pretreatment phase of the control system for the present invention.

If the treatment function 306 is selected, the control system, through the programmed software will automatically determine if treatment is appropriate and more particularly, if the light box 10 is prepared for treatment as shown in FIG. 20A. Thus, for example, if the system detects a failure in the light source, or a failure in one of the sensors or other equipment, treatment will not be enabled and would not proceed until the condition is remedied. If treatment is enabled however, the system will prompt the operator to input his or her unique identifier 314 and then request the input of container (i.e. biological fluid) information 316. Container information may be input manually or by scanning bar codes 222 on, for example, container 214 shown in FIG. 15. If treatment is appropriate, the system proceeds to the next function or phase as generally shown in FIG. 20B.

As shown in FIG. 20B, the control system displays additional options for the operator to select. For example, the operator may proceed to treatment of the container, request treatment of a second container or cancel the operation entirely as shown in step 320. If "Bag 2" option is selected, the operator is again requested to input container information 322 and the system will repeat the steps generally described above. If treatment on a single container is to be performed, the operator selects the treat function 324 which is generally shown in FIG. 20B and described in more detail below.

Figure 21:
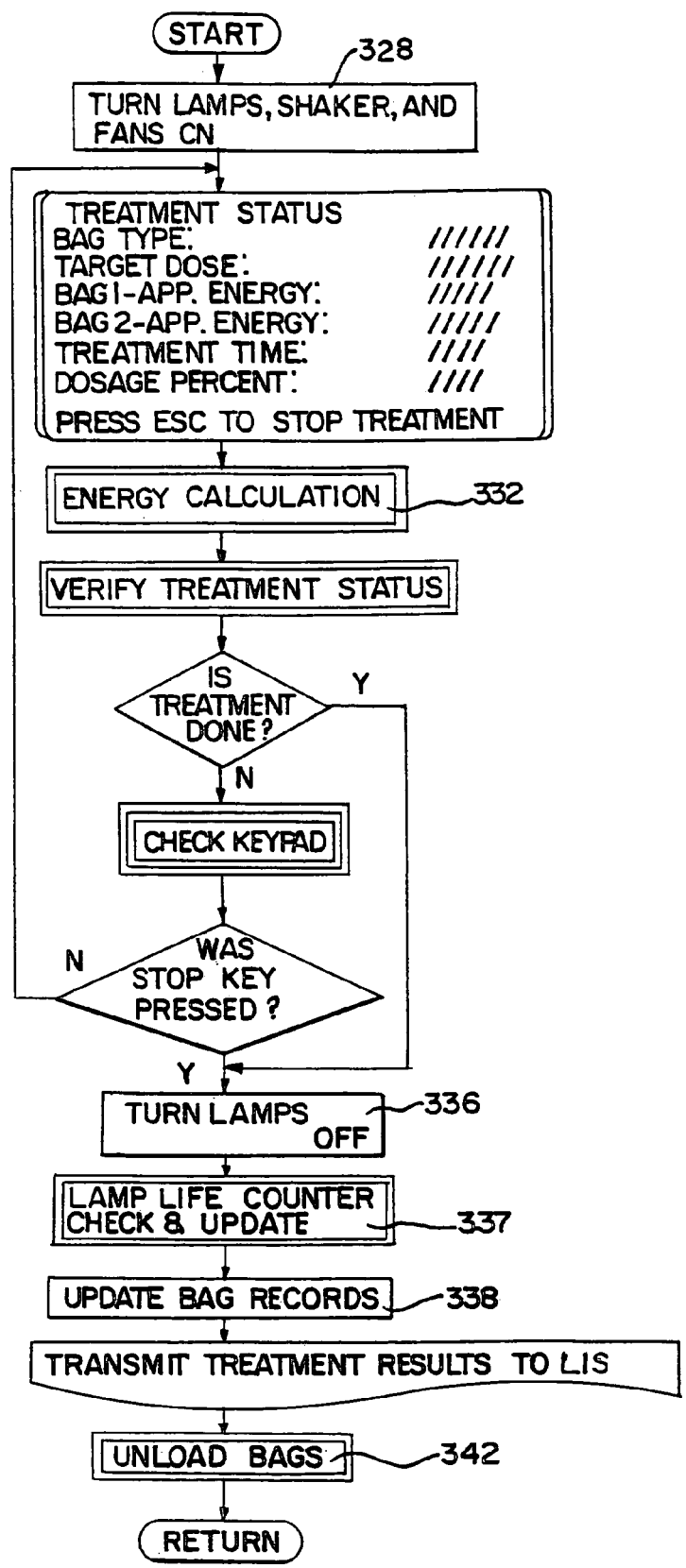
FIG. 21 is a flow chart showing the treatment phase of the control system for the present invention.

After containers have been placed into tray 90, to commence treatment the system activates the light source(s) 100, shaker motor 92 and fans as shown in step 328 of FIG. 21. The instrument may display, for verification by the operator, information regarding the fluid to be treated and the treatment process generally. For example, in one embodiment, the instrument may display, the predetermined target dose of energy to be applied to containers, the selected treatment time and a running value of the dosage percent being applied to the biological fluid during the treatment as shown in 330. Treatment will continue unless terminated by the operator or automatically terminated by the instrument in response to an alarm condition.

In one embodiment, container may be marked by markers 76 at the beginning of treatment and after treatment is completed. The marks made by marker 76 obliterate or otherwise masks the bar code, making it unreadable. Thus, a container with two masked bar codes 224 indicates that treatment has been successfully completed. On the other hand, if only one of the bar codes 224 has been masked, this serves as an indication that treatment was not successfully completed and the container may have to be discarded. Masking of bar codes 224 by markers 76 also ensures that a treated container will not be treated again.

During treatment, the system performs an energy calculation 332 which is computed by multiplying the light intensity sensor readings by preselected calibration factors, averaging the readings across the sensors in the same chamber and plane and adding the reading received for planes in the same chamber. The control system further verifies the treatment status 334. If treatment is completed, the system will automatically turn off lamps 100 as shown in 336.

The system may automatically update information on the lamp life as shown in 337 and update container records 338. Control system may continue to power shaker motor 92 until terminated. The results may be transmitted to a central computer 502 (FIG. 14). After treatment, the system will prompt the operator to unload containers 342 and may prompt the user to perform another treatment, if desired, as shown in 325 in FIG. 20B. The process may be repeated as generally described above.

Treatment time and energy dosage will vary depending on the biological fluid to be treated. For example, the treatment time may be at least one minute but may also be less than one minute. Where light box 10 is used for the pathogen inactivation of biological fluid, the treatment may typically be anywhere between 1-30 minutes. For example, for the pathogen inactivation of blood platelets, treatment is typically between 1-10 minutes, but more typically approximately 3-4 minutes. For the pathogen inactivation of blood plasma, treatment may also preferably be approximately 3-4 minutes.

Energy per unit area, or energy flux, is the product of power per unit area or, in the case of radiant flux, at the target, and the time of exposure. Accordingly, the amount of energy per unit area delivered to the target (for example, in one embodiment, the biological fluid) will vary with the duration of exposure and the irradiance—the radiant power per unit area incident on the target. In one embodiment the total radiant energy flux delivered may be between approximately 1-100 J/cm2 measured across a wavelength range of between approximately 400-700 nm. In another embodiment, where the light source provides light generally in the ultraviolet range, the total radiant energy flux delivered to the biological fluid may preferably be between 1-20 Joules/cm$^2$ measured across a wavelength range of between approximately 320-400 nm. In one specific embodiment, the total radiant energy flux delivered to blood platelets or blood plasma may be between approximately 1-5 J/cm2 and more typically approximately 3-4 J/cm$^2$ measured across a wavelength range of between approximately 320-400 nm. Preferably, the energy should not be outside the predetermined range in that excess heat generated within fluid treatment chamber 40 is to be avoided. For light treatment of blood platelets and blood plasma, for example, temperature within chamber 40 should typically not exceed 37° C. If an external temperature sensor of the type described above is used, the ambient temperature should be between 18°-30° C.

During treatment, tray 90 is preferably agitated at a preset frequency. Of course, the frequency should not be so great so as to harm the biological fluid or components thereof. Typically, the tray 90 may be agitated between approximately 50-100 cycles/min and for blood platelets, more preferably, between approximately 55-80 cycles/per minute. A cycle is defined as one complete back and forth oscillation of drawer 80.

Once treatment has been successfully completed, fluid from container 206 may be transferred to container 210 by breaking frangible number 230b and opening the flow path between the containers 206 and 210 (FIG. 15). Once inside container 210, the biological fluid is allowed to contact the adsorbent material for a selected period of time. As noted above, in one embodiment, container 210 may also include time-sensitive tabs 209 which change color over time. This way, the operator will know if the container has been in contact with the adsorbent material for the appropriate period of time. The adsorbent material is selected to remove any residual photochemical agent or any by products of the photochemical process that may have been included in the biological fluid. The adsorbent material may include polystyrene beads or activated charcoal or other adsorbent material. Such materials are described in greater detail in International Publication No. WO 96/40857, incorporated by reference herein.

Alternatively, in the disposable processing set 240 shown in FIG. 16, the biological fluid may simply pass-through container 246 without residing for any significant time, within the container. The details of the removal process and materials used are described in the above-identified International Publication No. WO96/40857.

The residence time, if any, of the biological fluid in container 210 (or 246) will be anywhere between approximately 30 seconds and 7 days. In addition, during contact of the biological fluid with the adsorbent material of container 210, it may be desirable to shake or otherwise agitate container 210 to ensure maximum contact with the adsorbent material.

Regardless of which disposable set is used, after the required residence time, if any, the biological fluid may be transferred to container 214 (or 248 in FIG. 16) by breaking frangible member 230C where it may be stored prior to transfusion to a recipient. Label 216 (or 249) applied to storage container 214 (or 248) now carries identifying information regarding the donor and the fluid. Masked bar codes 224 (or 251) indicate successful treatment of the biological fluid and that no additional treatment is required. The container may be severed and sealed from the remaining portion of the disposable processing set as generally described above.

Figure 22:
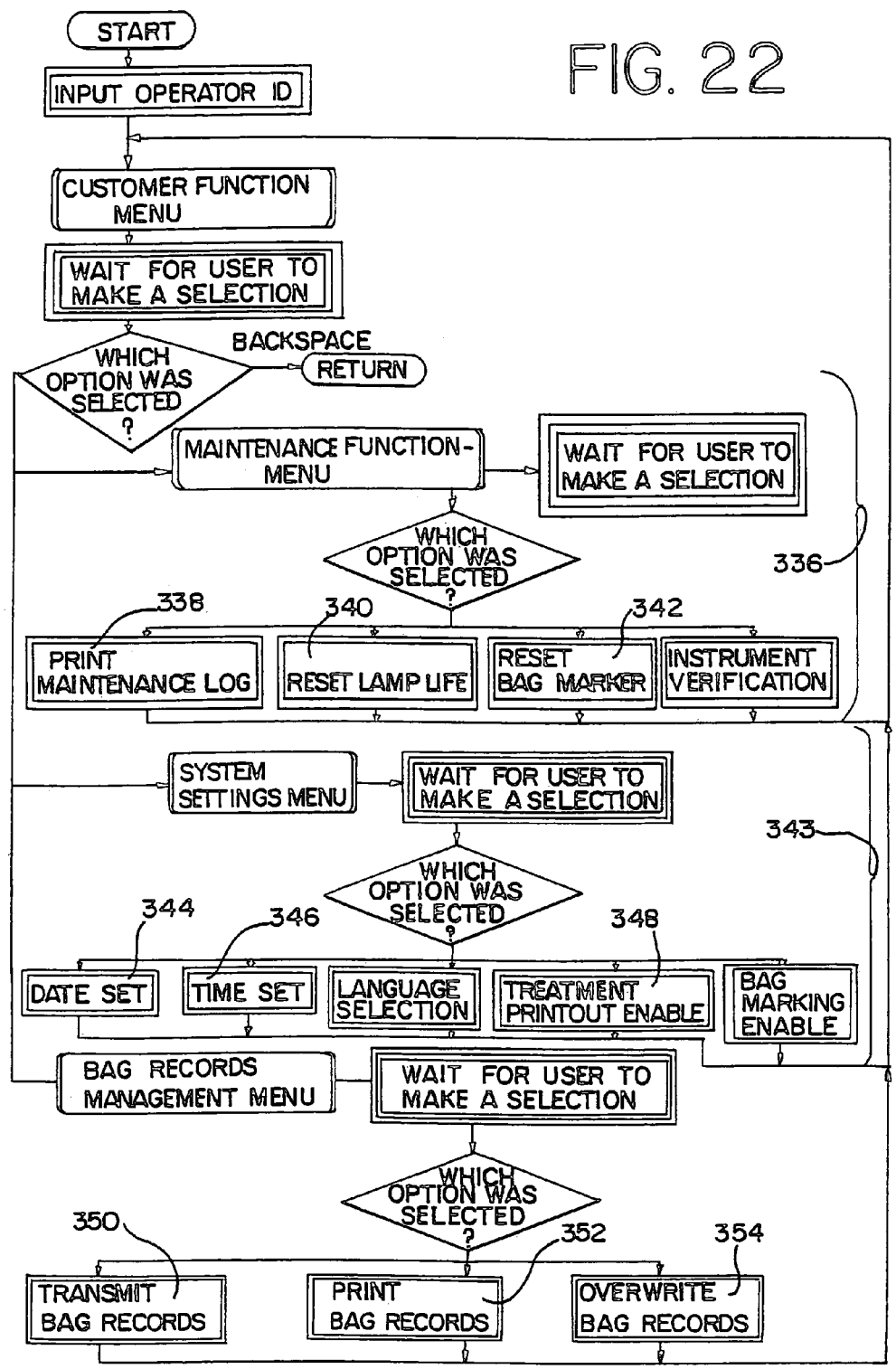
FIG. 22 is a flow chart showing the operator initiated instrument settings functions of the control system for the present invention.

In addition to the treatment function generally described above, the control system may prompt the operator to perform other functions such as the maintenance function 336 which may include printing a maintenance log 338, resetting lamp hours 340 resetting bag marker count 342. The operator may also select a system settings function 343 which allows the operator to set dates, times, languages 344,346,348. Finally, the control system may allow the operator to perform certain container management functions such as transmitting or printing container records or overwriting container records 350, 352, 354 as generally depicted in FIG. 22.

Figure 23:
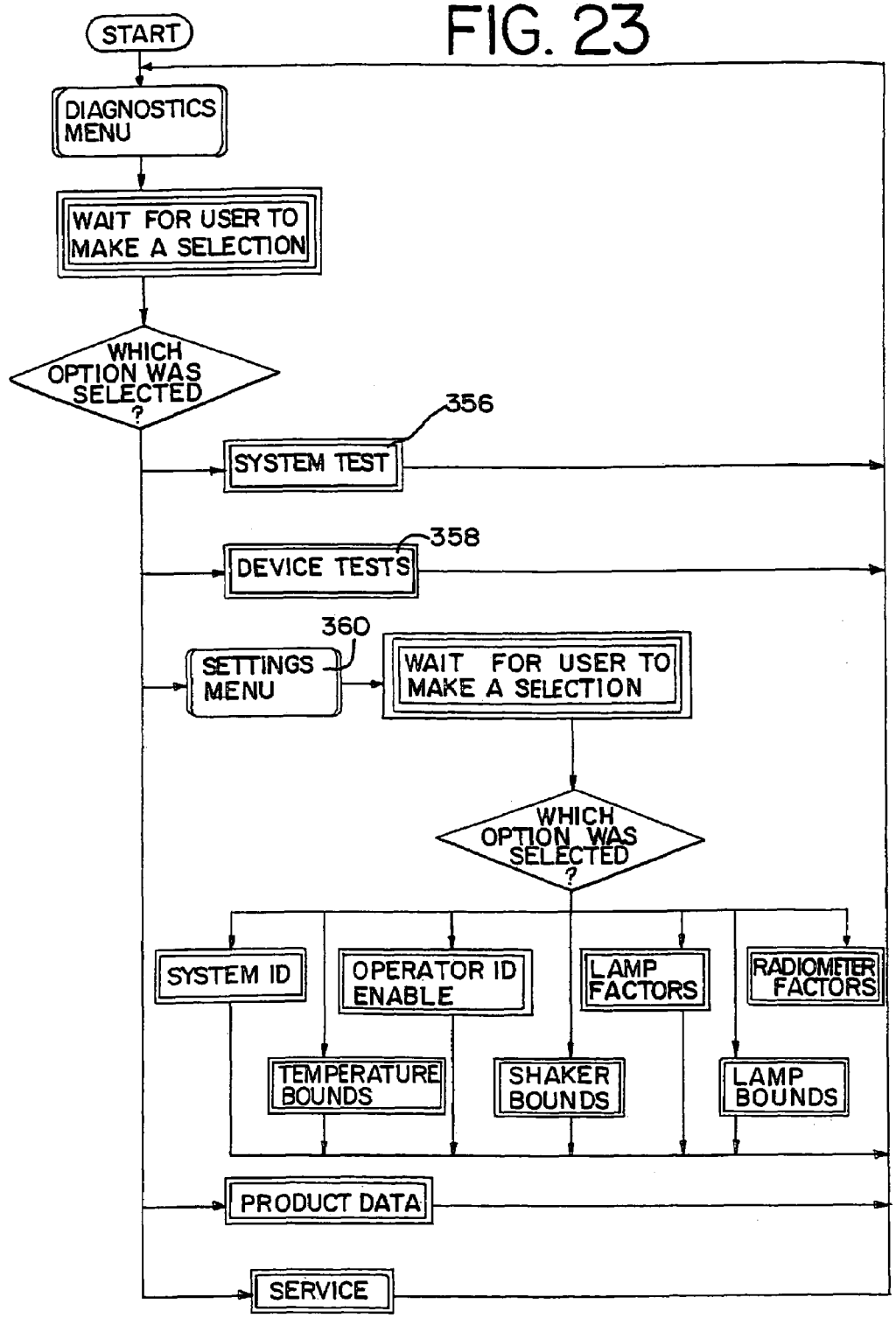
FIG. 23 is a flow chart showing the diagnostic functions of the control system for the present invention.

Alternatively, the diagnostics function shown in general in FIG. 23 may be selected. Selecting the diagnostics function allows the instrument to perform system tests 356, device tests 358 or provides the operator with a settings menu 360 to select (or change) system identification settings, temperature parameters, shaker parameters, lamp parameters, radiometer parameters, lamp factors and light as generally depicted in FIG. 23.

It will be appreciated that various modifications of the embodiments and methods described herein are possible in accordance with the scope of the present invention which are set forth in the appended claims.

That which is claimed:

1. A pre-assembled disposable fluid processing set for use in a photoactivation treatment of a biological fluid comprising:

a first container with a photochemical agent contained therein, said container being adapted for joinder to a source container of biological fluid and being enclosed within an overwrap that is impermeable to light of a selected photoactivating wavelength range;

a second container downstream of and pre-attached to said first container for holding the biological fluid and the photochemical agent during a photoactivation treatment, wherein said container is made of a material that is substantially translucent to light in the photoactivating wavelength range;

a sealed but openable flow path between said first and second containers;

a flow-through device downstream of and pre-attached to said second container for receiving at least said biological fluid from said second container, said device including adsorbent material for removing at least one or both of excess photochemical agent and photoactivation by-products from said biological fluid;

a sealed but openable flow path between said second container and said flow through device;

a container downstream of and pre-attached to said device for receiving said biological fluid from said device.

2. The disposable processing set of claim 1 comprising a tubing segment including an openable flow path for establishing flow communication between said device and said container downstream of said device.

3. The disposable fluid processing set of claim 1 wherein said overwrap is impermeable to light in the UVA wavelength range.

4. The disposable fluid processing set of claim 1 wherein said second container is made of a material that is substantially translucent to photoactivating light in the UVA range.

5. The disposable processing set of claim 1 further including a holder for temporarily holding at least said device.

6. The disposable processing set of claim 1 including a holder for temporarily holding said device and container downstream of said device.

7. The disposable fluid processing set of claim 1 wherein said openable flow paths include frangible connectors.

8. The disposable fluid processing set of claim 7 wherein said openable flow paths comprise plastic tubes with said frangible connectors disposed therein.

* * * * *